United States Patent
Cheng et al.

(10) Patent No.: US 11,884,632 B2
(45) Date of Patent: Jan. 30, 2024

(54) PREPARATION METHOD OF CAPROLACTAM

(71) Applicant: ZHEJIANG HENGYI PETROCHEMICAL RESEARCH INSTITUTE CO., LTD., Hangzhou (CN)

(72) Inventors: Shibiao Cheng, Zhejiang (CN); Songlin Wang, Zhejiang (CN); Xi Li, Zhejiang (CN); Han Wang, Zhejiang (CN); Fei Shen, Zhejiang (CN); Xinping Zhang, Zhejiang (CN); Zhaobin Jiang, Zhejiang (CN); Zhimin Hu, Zhejiang (CN)

(73) Assignee: ZHEJIANG HENGYI PETROCHEMICAL RESEARCH INSTITUTE CO., LTD., Hangzhou (CN)

( * ) Notice: Subject to any disclaimer, the term of this patent is extended or adjusted under 35 U.S.C. 154(b) by 282 days.

(21) Appl. No.: 17/212,530

(22) Filed: Mar. 25, 2021

(65) Prior Publication Data
US 2022/0064124 A1    Mar. 3, 2022

(30) Foreign Application Priority Data
Sep. 2, 2020 (CN) .......................... 202010911945.4

(51) Int. Cl.
| | | |
|---|---|---|
| C07D 223/10 | (2006.01) | |
| C07D 201/06 | (2006.01) | |
| C07D 201/16 | (2006.01) | |
| B01J 29/70 | (2006.01) | |
| B01J 35/08 | (2006.01) | |
| B01J 37/00 | (2006.01) | |
| B01J 37/04 | (2006.01) | |
| B01J 37/08 | (2006.01) | |

(52) U.S. Cl.
CPC ............ *C07D 223/10* (2013.01); *B01J 29/70* (2013.01); *B01J 35/08* (2013.01); *B01J 37/0036* (2013.01); *B01J 37/04* (2013.01); *B01J 37/08* (2013.01)

(58) Field of Classification Search
CPC ... C07D 223/10; C07D 201/06; C07D 201/16
See application file for complete search history.

(56) References Cited

U.S. PATENT DOCUMENTS

| | | | |
|---|---|---|---|
| 4,709,024 A | 11/1987 | Sato et al. | |
| 4,717,769 A | 1/1988 | Sato et al. | |

FOREIGN PATENT DOCUMENTS

| | | | |
|---|---|---|---|
| CN | 101429149 A | 5/2009 | |
| CN | 101429148 B | 8/2012 | |
| CN | 103508954 B | 8/2016 | |
| CN | 109574928 A | 4/2019 | |
| CN | 109718828 A | 5/2019 | |
| CN | 109772426 A | 5/2019 | |
| CN | 109833898 A | 6/2019 | |

OTHER PUBLICATIONS

Hiroshi Ichihashi, "10 Vapor Phase Beckmann Rearrangement over a High Silica MFI Zeolite" Studies in Surface Science and Catalysis, 2003, pp. 73-78, vol. 145.

Hiroshi Ichihashi et al., "Some aspects of the vapor phase Beckmann rearrangement for the production of ε-caprolactam over high silica MFI zeolites", Catalysis Today, Apr. 2002, pp. 23-28, vol. 73.

Zong Baoning et al., "Green Production Technology of the Monomer of Nylon-6: Caprolactam", Engineering, Jun. 2017, pp. 379-384, vol. 3.

Science China Chemistry in Chinese Edition, 2014, pp. 40-45, vol. 44.

*Primary Examiner* — Brenda L Coleman
(74) *Attorney, Agent, or Firm* — Sughrue Mion, PLLC

(57) ABSTRACT

The present disclosure discloses a method for preparing caprolactam including: (1) contacting cyclohexanone oxime with a catalyst to carry out reaction in the presence of ethanol and under the condition of gas phase Beckmann rearrangement reaction of cyclohexanone oxime; (2) separating the reaction product obtained in step (1) to produce an ethanol solution of crude caprolactam, and then separating the ethanol solution of crude caprolactam to obtain ethanol and crude caprolactam; (3) removing impurities with boiling points lower than that of caprolactam in the crude caprolactam to obtain a light component removal product; (4) mixing the light component removal product with a crystallization solvent to carry out crystallization and solid-liquid separation to obtain a crystalline crystal; (5) subjecting the crystalline crystal to a hydrogenation reaction; wherein the crystallization solvent contains 0.1-2 wt % of ethanol.

21 Claims, No Drawings

PREPARATION METHOD OF CAPROLACTAM

CROSS REFERENCE TO RELATED APPLICATIONS

This application claims priority to the Chinese Application No. 202010911945.4, filed on Sep. 2, 2020, entitled "PREPARATION METHOD OF CAPROLACTAM", which is specifically and entirely incorporated by reference.

FIELD

The present disclosure relates to the field of caprolactam production, in particular to a preparation method of caprolactam.

BACKGROUND

Epsilon-caprolactam is one of important raw materials for synthetic fibers and synthetic resins, and is mainly used for the production of polyamide fibers (nylon 6), resins, films and the like. At present, the method for industrially producing caprolactam adopts the fuming sulfuric acid as a catalyst and a solvent, and carries out a liquid phase Beckmann rearrangement reaction in regard to the cyclohexanone oxime. However, the process has the defects such as corrosion of apparatus, environmental pollution, unsatisfactory economic benefit, and generating a large amount of byproduct ammonium sulfate.

The gas phase Beckmann rearrangement reaction of cyclohexanone oxime on a solid acid catalyst is a new process for producing Epsilon-caprolactam without generation of the ammonium sulfate, it has the advantages such as without causing corrosion of apparatus and environmental pollution, and the separation and purification of products are greatly simplified; as a result, the gas phase Beckmann rearrangement reaction process without generation of the ammonium sulfate has attracted great attention from by the industrial insiders.

In order to develop a solid acid catalyst suitable for a gas phase Beckmann rearrangement reaction, the researchers at home and abroad of the People's Republic of China (PRC) have implemented plentiful researches on two kinds of catalysts, namely an oxide (composite oxide) and a zeolite molecular sieve, the results show that most of the catalysts have certain activity, but the common disadvantages are that the catalysts are prone to deactivate, and the service life of the catalysts is short and cannot meet the requirements of industrialized production. In fact, catalyst deactivation is a common problem in gas phase Beckmann rearrangement reaction.

The Sumitomo Chemical Industry Co., Ltd. in Japan has implemented a lot of researches in regard to the gas phase Beckmann rearrangement reaction (U.S. Pat. No. 4,709,024, 1987; U.S. Pat. No. 4,717,769, 1988; Sci. Tech Catal. 2002, pp. 73-78; Catal. Today, 2002, No. 73, pp. 23-28) by using a high silicon MFI structure molecular sieve as a catalyst and adopting methanol as a solvent, and utilizing a fluidized bed continuous reaction-regeneration process, the problems of easy deactivation of the catalyst are solved, the conversion rate of cyclohexanone oxime is larger than 99%, the selectivity of caprolactam is greater than 95%, and the contents of the byproducts 5-cyano-1-pentene, 5-cyano-1-pentane, cyclohexanone and cyclohexenone are about 2%, 0.5%, 1% and 0.5%, respectively.

The SINOPEC Research Institute of Petroleum Processing (RIPP) has developed a fixed bed and moving bed process to carry out a gas phase Beckmann rearrangement reaction to generate epsilon-caprolactam (CN200710177011.7; CN200710177012.1; CN201210217072.2; *Engineering*, 2017, No. 3, pp. 379-384; *SCIENCE CHINA* Chemistry in the Chinese Edition: 2014, No. 44, pp. 40-45), wherein the conversion rate of the cyclohexanone oxime is larger than 99.5%, the selectivity of the caprolactam is close to 96%, and the contents of byproducts 5-cyano-1-pentene, 5-cyano-1-pentane, cyclohexanone and cyclohexenone are 1.0%, 0.5%, 0.5% and 0.4%, respectively.

The institutions committed to development of the gas phase Beckmann rearrangement reaction at home and abroad generally adopt methanol as a reaction solvent, the main reason may be that the methanol is safe and easily available, and can be readily recovered, and an azeotrope does not exist between methanol and water. However, the selectivity of caprolactam in the process still needs to be improved, and the technical economy of the whole process is still unsatisfactory.

The selectivity of caprolactam and the subsequent separation, purification and refining are very important sectors for the production of caprolactam, the selectivity of caprolactam affects the technical economy of caprolactam production, and the subsequent separation, purification and refining influence the product quality of caprolactam.

In summary, the industrial production of caprolactam in the prior art has the defects, namely the overall process economy of caprolactam production still have room for improvement, and the yield and quality of caprolactam need to be further improved.

SUMMARY

The present disclosure aims to overcome the problems of poor economic efficiency of caprolactam production and low yield and quality of caprolactam in the prior art, and provides a preparation method of caprolactam. The method has the characteristics of improved economic efficiency and higher yield and quality of caprolactam.

In order to achieve the above-mentioned objects, the present disclosure provides a method for preparing caprolactam, the method comprises the following steps:

(1) contacting cyclohexanone oxime with a catalyst to carry out reaction in the presence of ethanol and under the condition of gas phase Beckmann rearrangement reaction of cyclohexanone oxime;

(2) separating the reaction product obtained in step (1) to produce an ethanol solution of crude caprolactam, and then separating the ethanol solution of crude caprolactam to obtain ethanol and crude caprolactam;

(3) removing impurities with boiling points lower than that of caprolactam in the crude caprolactam to obtain a light component removal product;

(4) mixing the light component removal product with a crystallization solvent to carry out crystallization and solid-liquid separation to obtain a crystalline crystal;

(5) subjecting the crystalline crystal to a hydrogenation reaction;

wherein the crystallization solvent contains 0.1-2 wt % of ethanol.

Preferably, the preparation method of the catalyst comprises the following steps:

(a-1) mixing ethyl orthosilicate, ethanol, a metal source, tetrapropylammonium hydroxide with water to obtain a colloid mixture; wherein the molar ratio of ethyl orthosilicate calculated by $SiO_2$, ethanol, tetrapropylammonium hydroxide and water is 1:(4-25):(0.06-0.45):(6-100); the weight ratio of the ethyl orthosilicate calculated by $SiO_2$ relative to the metal source calculated by the metal element is (10,000-200,000):1;

(a-2) subjecting the colloid mixture to a two-stage crystallization with an ethanol-hydrothermal system under variable temperatures, wherein the conditions of the two-stage crystallization with an ethanol-hydrothermal system under variable temperatures comprise: crystallizing at 40-80° C. for 0.5-5 days, and crystallizing at 80-130° C. for 0.5-5 days;

(a-3) concentrating the crystallization mother liquor obtained in step (a-2) to obtain a molecular sieve slurry;

(a-4) blending the molecular sieve slurry with a binder and pulping to obtain a molecular sieve-binder slurry; subjecting the molecular sieve-binder slurry to a mist spray forming, and then roasting;

(a-5) contacting the roasted product of step (a-4) with an alkaline buffer solution of a nitrogen-containing compound, and subsequently carrying out drying.

Further preferably, the ethanol in the crystallization mother liquor of step (a-3) is recovered for providing at least part of the ethanol of step (1) and/or at least part of the ethanol in the crystallization solvent of step (4).

Preferably, the preparation method of the catalyst comprises the following steps:

(b-1) mixing ethyl orthosilicate, ethanol, a metal source, tetrapropylammonium hydroxide and water to obtain a colloid mixture; wherein the molar ratio of ethyl orthosilicate calculated by $SiO_2$, ethanol, tetrapropylammonium hydroxide and water is 1:(4-25):(0.06-0.45):(6-100); the weight ratio of the ethyl orthosilicate calculated by $SiO_2$ relative to the metal source calculated by the metal element is (10,000-200,000):1;

(b-2) subjecting the colloid mixture to a two-stage crystallization with an ethanol-hydrothermal system under variable temperatures, wherein the conditions of the two-stage crystallization with an ethanol-hydrothermal system under variable temperatures comprise: crystallizing at 40-80° C. for 0.5-5 days, and crystallizing at 80-130° C. for 0.5-5 days;

(b-3) sequentially filtering and drying the crystallization mother liquor obtained in step (b-2) to obtain a molecular sieve raw powder;

(b-4) crushing the molecular sieve raw powder, blending the crushed molecular sieve raw powder with a binder, and then carrying out rotary molding to obtain spherical particles;

(b-5) roasting the spherical particles, contacting the roasted spherical particles with an alkaline buffer solution containing a nitrogen compound, and subsequently carrying out drying.

Further preferably, the ethanol in the crystallization mother liquor of step (b-3) is recovered for providing at least part of the ethanol of step (1) and/or at least part of the ethanol in the crystallization solvent of step (4).

The inventors of the present disclosure have discovered in the research process that the methanol is used in the prior art as a solvent for a majority of the gas phase Beckmann rearrangement reactions of cyclohexanone oxime; in fact, methanol with one carbon atom is relatively active when the methanol is subjected to a high-temperature catalytic reaction in the presence of a catalyst, methanol is more prone to causing side reactions and generating a variety of methyl-containing byproducts. The presence of a large amounts of dimethyl ether, trimethylamine is found in the gaseous phase product; the diverse methyl-containing byproducts are formed in a methanol solution of caprolactam, the methyl-containing byproducts comprise: 2-methylcyclopentanone, 3-methoxy-cyclohexanone, N-methyl-aniline, methyl-caprolactam, N-methyl-caprolactam, O-methyl-epsilon-caprolactam imide; the methanol solution of caprolactam further comprise a trace amount of methyl by-products such as 2-methacrylonitrile, 4-methylvaleronitrile, 2-methylpyridine, 5-hexenoic acid methyl ester, 1-methoxy-1,3-cyclohexadiene, 4-hexenoic acid methyl ester, 1-methoxy-1,4-cyclohexadiene, N,N-dimethylaniline, 2,5-dimethylaniline, 2,6-dimethylaniline, 2-methylaniline and other compounds. Among the byproducts, the distribution of the products is extremely unsatisfactory, and the boiling points of the by-products are close to that of caprolactam, such a circumstance is not favorable for the subsequent separation, purification and refinement of crude caprolactam.

The preparation method of caprolactam provided by the present disclosure adopts specific steps, and ethanol is used as both a solvent of gas phase Beckmann rearrangement reaction of cyclohexanone oxime and a crystallization solvent in a crystallization process, so that the stability of the catalyst is improved, the selectivity of caprolactam is higher, and the types and the content of byproducts are reduced, thus it is more beneficial to improving the yield and quality of caprolactam. Preferably, the catalyst preparation process (molecular sieve synthesis process) associated with the present disclosure also uses ethanol, which not only can enhance stability of the catalyst and further improve the yield and quality of caprolactam, but also can recover ethanol in the catalyst preparation process for providing at least part of ethanol in step (1) and/or at least part of ethanol in the crystallization solvent in step (4), thereby further improving the economy of the whole process.

DETAILED DESCRIPTION

The terminals and any value of the ranges disclosed herein are not limited to the precise ranges or values, such ranges or values shall be comprehended as comprising the values adjacent to the ranges or values. As for numerical ranges, the endpoint values of the various ranges, the endpoint values and the individual point value of the various ranges, and the individual point values may be combined with one another to produce one or more new numerical ranges, which should be deemed have been specifically disclosed herein.

In a first aspect, the present disclosure provides a method for preparing caprolactam, the method comprises the following steps:

(1) contacting cyclohexanone oxime with a catalyst to carry out reaction in the presence of ethanol and under the condition of gas phase Beckmann rearrangement reaction of cyclohexanone oxime;

(2) separating the reaction product obtained in step (1) to produce an ethanol solution of crude caprolactam, and then separating the ethanol solution of crude caprolactam to obtain ethanol and crude caprolactam;

(3) removing impurities with boiling points lower than that of caprolactam in the crude caprolactam to obtain a light component removal product;

(4) mixing the light component removal product with a crystallization solvent to carry out crystallization and solid-liquid separation to obtain a crystalline crystal;

(5) subjecting the crystalline crystal to a hydrogenation reaction;

wherein the crystallization solvent contains 0.1-2 wt % of ethanol.

According to the method provided by the present disclosure, ethanol is used as a solvent in the gas phase Beckmann rearrangement reaction. According to a preferred embodiment of the present disclosure, the cyclohexanone oxime in step (1) accounts for 20-50 wt %, preferably 35-45 wt %, of the sum of cyclohexanone oxime and ethanol.

According to the present disclosure, it is preferable that the reaction in step (1) is performed in the presence of ethanol and water. The amount of water is selected within a wide range, and preferably water accounts for 0.1-3 wt %, more preferably 0.2-1 wt %, of the total amount of water, ethanol and cyclohexanone oxime.

According to a specific embodiment of the present disclosure, the reaction is performed in the presence of a carrier gas. The carrier gas may remove the reaction heat. Preferably, an inert gas is used as a carrier gas in the reaction of step (1), and the molar ratio of the inert gas relative to cyclohexanone oxime is 0.5-50:1, preferably 1-30:1, more preferably 1-10:1.

Preferably, the inert gas is at least one selected from the group consisting of nitrogen gas, helium gas, argon gas and neon gas, and more preferably nitrogen gas.

According to the present disclosure, it is preferable that the conditions of gas phase Beckmann rearrangement reaction comprise: the temperature is within a range of 350-400° C., preferably 360-400° C.; the pressure is within a range of 0.005-0.8 MPa, preferably 0.05-0.5 MPa; the weight hourly space velocity of the cyclohexanone oxime is within a range of 0.1-10 $h^{-1}$, preferably 0.3-8 $h^{-1}$.

According to the present disclosure, the conversion of cyclohexanone oxime in the reaction of step (1) is not lower than 99.5 wt %, preferably not lower than 99.8 wt %. By adopting the preferred embodiment, the cyclohexanone oxime is substantially or completely converted, the energy consumption of the subsequent separation can be favorably reduced.

The catalyst in step (1) is selected within a wide range of the present disclosure, and it may be a catalyst which is conventionally used in the field and can be used for gas phase Beckmann rearrangement reaction of cyclohexanone oxime. In order to further improve the conversion rate of cyclohexanone oxime and the selectivity of caprolactam, it is preferable that the catalyst comprises a binder and a silicon molecular sieve having a MFI topological structure; the catalyst comprises 50-95 wt % of the molecular sieve based on the dry weight and 5-50 wt % of the binder in terms of oxide, based on the dry weight of the catalyst.

The molecular sieve contains metal elements, and ions of the metal elements have a Lewis acid characteristic; the content of the metal element in the molecular sieve is 5-100 µg/g, based on the total amount of the molecular sieve.

The ions of the metal elements have a Lewis acid characteristic, which means that the ions of the metal elements can accept electron pairs.

It should be noted that the metal elements is contained in the silicon molecular sieve having a MFI topological structure of the present disclosure in a very trace amount, and it can be concluded that a trace amount of metal elements exist in the molecular sieve framework in the form of metal ions.

In the silicon molecular sieve having a MFI topological structure of the present disclosure, metal elements are presented on a molecular sieve framework in the form of metal cations.

In the present disclosure, the content of the metal elements is measured by using an inductively coupled plasma (ICP) atomic emission spectrometer 7000DV, manufactured by PE (Perkin Elmer Incorporation) of the Unites States of America (USA), under the test conditions as follows: the molecular sieve is dissolved by using HF acid or aqua regia to completely dissolve silicon oxide and metal oxide in the sample, and the content of metal ions is measured in the aqueous solution.

The present disclosure provides wide selection ranges of the contents of silicon element and oxygen element in the molecular sieve, and in a specific embodiment, the sum of the contents of the silicon element, the oxygen element and the metal elements in the molecular sieve is 100 percent based on the total amount of the molecular sieve.

According to a preferred embodiment of the present disclosure, the content of the metal elements in the molecular sieve is 6-90 µg/g, preferably 30-80 µg/g, based on the total amount of the molecular sieve. Specifically, for example, the content may be 30 µg, 35 µg/g, 40 µg, 45 µg/g, 50 µg, 55 µg, 60 µg, 70 µg/g, 75 µg/g, 80 µg/g, or any value within a range formed by any two of the numerical values. In the preferred embodiment, the catalyst has better catalytic performance, and it is more conducive to improving the conversion rate of cyclohexanone oxime and the selectivity of caprolactam. In the present disclosure, if the content of the metal elements is excessively high, the Lewis acid characteristic of the molecular sieve is possibly enhanced, such that the unnecessary side reactions are induced, which is not favorable to improve selectivity of caprolactam; however, if the content of the metal elements is deficient, it is not conducive to prolonging service life of the catalyst and improving stability of the catalyst.

In the present disclosure, each of the metal elements whose ions have a Lewis acid characteristic may be used therein, and preferably, the metal element is at least one selected from the group consisting of transition metal elements, group IIIA elements and group IVA elements. Preferably, the transition metal element is at least one selected from the group consisting of group IB, group IIB, group IVB, group VB, group VIB, group VIIB, and group VIII metal elements.

According to a preferred embodiment of the present disclosure, the metal element is at least one selected from the group consisting of elements Al, Ga, Ge, Ce, Ag, Co, Ni, Cu, Zn, Mn, Pd, Pt, Cr, Fe, Au, Ru, Rh, Ti, Zr, V, Mo and W.

Further preferably, the metal elements have an ionic valence of +3 (trivalent) and/or an ionic valence of +4 (tetravalent). The inventors of the present disclosure have discovered in the research process that the metal elements have an ionic valence of +3 (tetravalent) and/or an ionic valence of +4 (tetravalent) is more favorable for the metal element to enter the molecular sieve framework and more conducive to charge balance.

According to the present disclosure, the metal element is further preferably at least one selected from the group consisting of elements Fe, Al, Ga, Ge, Cr, Ti, Zr, and Ce. In the preferred embodiment, it is more advantageous to improve the performance of the catalyst, thereby improving conversion rate of cyclohexanone oxime and the selectivity of caprolactam.

According to the present disclosure, it is preferable that the molecular sieve has a BET specific surface area within a range of 400-500 $m^2/g$, more preferably 420-450 $m^2/g$. In the preferred circumstance, it is more advantageous to improve the performance of the molecular sieve as a catalyst.

The present disclosure has wide selection ranges of the external specific surface area of the molecular sieve, it is preferable that the external specific surface area of the molecular sieve is within a range of 30-60 m²/g, more preferably 35-50 m²/g. In the present disclosure, the BET specific surface area and the external specific surface area of the molecular sieve are determined by the $N_2$ adsorption-desorption method, specifically, are measured by an automatic adsorption apparatus with a model number Micromeritics ASAP-2460 manufactured in the USA, under the following test conditions: $N_2$ is used as an adsorbate, the adsorption temperature is −196.15° C. (liquid nitrogen temperature), and degassing is performed at 1.3 Pa and the constant temperature 300° C. for 6 hours.

The selection range of the crystalline grain particle size of the molecular sieve is wide, and it is preferable that the crystalline grain particle size of the molecular sieve is within a range of 0.1-0.3 μm, further preferably 0.1-0.25 μm, and more preferably 0.1-0.2 μm. In the preferred circumstances, it is more advantageous to improve the catalytic performance of the molecular sieve as a catalyst. In the present disclosure, the crystalline grain particle size of the molecular sieve is measured with a field emission type scanning electron microscope with a model number S-4800 manufactured by the Hitachi Corporation in Japan.

According to a preferred embodiment of the present disclosure, the binder is silicon oxide.

The preparation method, the particle size and the shape of the catalyst of the present disclosure are selected in wide ranges, and those skilled in the art can make suitable choices according to a specific reactor for performing the gas phase Beckmann rearrangement reaction of cyclohexanone oxime. For example, the gas phase Beckmann rearrangement reaction of cyclohexanone oxime may be carried out in any one of the group consisting of a fixed bed reactor, a radial movement bed reactor, a single-stage and multi-stage fluidized bed reactor, a reactor formed by combining a fluidized bed with a fixed bed, and a reactor formed by combining a fluidized bed with a radial movement bed, preferably a single-stage and multi-stage fluidized bed reactor. Preferably, the gas phase Beckmann rearrangement reaction of cyclohexanone oxime is carried out in a fixed bed reactor, and the catalyst is in a strip-type (it can be obtained by extrusion molding) or a spherical shape (it can be obtained by rotary molding) and has a diameter within a range of 1-3 mm. Preferably, the gas phase Beckmann rearrangement reaction of cyclohexanone oxime is performed in a moving bed reactor, the catalyst is in a spherical shape, and the particle size of the catalyst is within a range of 0.5-3 mm, preferably 0.8-2.5 mm (it can be obtained by rotary molding). Preferably, the gas phase Beckmann rearrangement reaction of cyclohexanone oxime is carried out in a fluidized bed reactor, the catalyst is in a microsphere, and the particle size of the catalyst is within a range of 20-200 μm, preferably 40-150 μm (it can be obtained by mist spray forming).

In order to increase the conversion rate of cyclohexanone oxime, the fluidized bed reactor and the fixed bed reactor are connected in series as an example in an illustrative description of the examples of the present disclosure. The present disclosure is not limited thereto, as long as it is conducive to ensuring the conversion rate of cyclohexanone oxime. When two reactors connected in series are used in the present disclosure, the amount of catalyst to be loaded in each reactor and the shape of the catalyst to be loaded are not particularly limited, and the shape of the catalyst to be loaded may be appropriately selected depending on the type of the reactor. Preferably, the weight ratio of the catalyst loaded in the preceding reactor relative to the catalyst loaded in the rear reactor along the direction of material flow is within a range of 5-15:1.

According to a preferred embodiment of the present disclosure, the synthesis of the silicon molecular sieve having a MFI topological structure is carried out under the ethanol-containing condition.

According to a preferred embodiment of the present disclosure (mist spray forming), the catalyst comprises 50-80 wt % of the molecular sieve based on the dry weight and 20-50 wt % of the binder in terms of oxide, based on the dry weight of the catalyst. Further preferably, the preparation method of the catalyst comprises the following steps:

(a-1) mixing ethyl orthosilicate, ethanol, a metal source, tetrapropylammonium hydroxide with water to obtain a colloid mixture; wherein the molar ratio of ethyl orthosilicate calculated by $SiO_2$, ethanol, tetrapropylammonium hydroxide and water is 1:(4-25):(0.06-0.45):(6-100); the weight ratio of the ethyl orthosilicate calculated by $SiO_2$ relative to the metal source calculated by the metal element is (10,000-200,000):1;

(a-2) subjecting the colloid mixture to a two-stage crystallization with an ethanol-hydrothermal system under variable temperatures, wherein the conditions of the two-stage crystallization with an ethanol-hydrothermal system under variable temperatures comprise: crystallizing at 40-80° C. for 0.5-5 days, and then crystallizing at 80-130° C. for 0.5-5 days;

(a-3) concentrating the crystallization mother liquor obtained in step (a-2) to obtain a molecular sieve slurry;

(a-4) blending the molecular sieve slurry with a binder and pulping to obtain a molecular sieve-binder slurry; subjecting the molecular sieve-binder slurry to a mist spray forming, and then roasting;

(a-5) contacting the roasted product of step (a-4) with an alkaline buffer solution of a nitrogen-containing compound, and subsequently carrying out drying.

Unless otherwise specified in the present disclosure, the molar ratio and the weight ratio of the materials in the preparation process of catalyst refer to the molar ratio and the weight ratio of the used amount when the materials are fed (batch charged).

According to a preferred embodiment of the present disclosure, the preferred preparation method of catalyst of the present disclosure does not contain an addition of an organic amine. In the preferred embodiment, the catalyst has better performance. In the present disclosure, tetrapropylammonium hydroxide is used as an organic base and can also be used as a template agent, and the addition of an organic amine is not required. In the present disclosure, the organic amine refers to at least one of aliphatic amine compounds, and for example, it may be at least one of the group consisting of mono-n-propylamine, di-n-propylamine, tri-n-propylamine, ethylamine, n-butylamine, ethylenediamine and hexamethylenediamine.

According to a preferred embodiment of the present disclosure, the molar ratio of ethyl orthosilicate calculated by $SiO_2$, ethanol, tetrapropylammonium hydroxide and water is 1:(4-15):(0.06-0.3):(15-50), more preferably 1:(6-14):(0.1-0.25):(20-40). In the preferred embodiment, the prepared catalyst has better catalytic performance.

According to a preferred embodiment of the present disclosure, the weight ratio of ethyl orthosilicate calculated by $SiO_2$ relative to the metal source calculated by metal element is (10,000-100,000):1, more preferably (15,000-50,000):1.

According to the method provided by the present disclosure, the selection of the metal element in the metal source is as previously mentioned, and the content is not repeated here.

The present disclosure has a wide range of choices for the metal source, which may be a compound containing various metal elements and being capable of providing the above metal elements, and the compound containing the metal elements is preferably soluble. In the present disclosure, the term "soluble" means that the compound is capable of being dissolved in a solvent directly or in the presence of a co-solvent, and the solvent is preferably water.

According to the present disclosure, the metal source is preferably at least one selected from the group consisting of a nitrate of the metal, a chloride of the metal, a sulfate of the metal, an acetate of the metal, and an ester metal compound. In a specific embodiment, the ester metal compound is tetraethyl titanate and/or tetrabutyl titanate.

According to a preferred embodiment of the present disclosure, when the metal is an element Al, the metallic aluminum source may also be a compound in the form of alumina, such as SB powder, V250, and pseudo-boehmite.

According to a preferred embodiment of the present disclosure, the metal source is preferably at least one selected from the group consisting of $Fe(NO_3)_3$, $Ni(NO_3)_2$, tetrabutyl titanate, $Pd(NO_3)_2$, $Ce(NO_3)_4$, $Al(NO_3)_3$, $Cu(NO_3)_2$, $ZrOCl_2$, $Ga(NO_3)_3$, $H_2PtCl_6$ and $Cr(NO_3)_3$, and is further preferably at least one selected from the group consisting of $Fe(NO_3)_3$, tetrabutyl titanate, $Al(NO_3)_3$, $Ga(NO_3)_3$ and $Cr(NO_3)_3$. The metal source may contain crystal water or does not contain crystal water, and the present disclosure is not particularly limited thereto.

The order of mixing in step (a-1) is not particularly limited in the present disclosure, as long as the colloid mixture can be obtained, any two of them may be initially mixed and then blended with the rest of the substances, or any three of them may be initially mixed and then blended with the rest of the substances. Preferably, it is desirable to avoid gel formation during the process of adding materials and to prevent excessive temperature rise of the liquid phase during the process of adding materials. Specifically, for example, the ethanol and tetrapropylammonium hydroxide may be mixed, water and a metal source may be then added, and the ethyl orthosilicate may be subsequently added; or the ethanol and tetrapropylammonium hydroxide may be mixed, water and ethyl orthosilicate are sequentially added, and a metal source is then added; or the ethyl orthosilicate, ethanol and tetrapropylammonium hydroxide may be mixed, the water and the metal source are sequentially added; alternatively, the ethyl orthosilicate, ethanol, tetrapropylammonium hydroxide may be mixed, water is then added, and a metal source is subsequently added. In the present disclosure, the metal source may be introduced alone or in the form of a solution.

According to the present disclosure, the mixing process of step (a-1) preferably comprises: ethanol and tetrapropylammonium hydroxide are mixed, ethyl orthosilicate is then added, water and a metal source are subsequently added.

The specific operation selection ranges for the mixing in the present disclosure are wide, and according to a preferred embodiment of the present disclosure, the mixing is performed under the stirring conditions. In the present disclosure, the stirring time is not particularly limited, so long as the colloid mixture can be obtained. For example, the mixture may be stirred at room temperature (25° C.) for 2-6 hours.

According to a preferred embodiment of the present disclosure, the conditions of the two-stage crystallization with an ethanol-hydrothermal system under variable temperatures comprise: crystallizing at 50-80° C. for 1-1.5 days, and crystallizing at 100-120° C. for 1-3 days. Under the preferred embodiment, the utilization rate of crystallization raw materials is further improved, and the prepared catalyst containing the molecular sieve has better catalytic performance under the specific crystallization conditions. In the present disclosure, the two-stage crystallization with an ethanol-hydrothermal system under variable temperatures is preferably performed in a closed system under an autogenous pressure, for example, in an airtight reaction kettle.

According to the present disclosure, the crystallization mother liquor preferably has a pH greater than 11, preferably not less than 13, for example between 13 and 14.

In the present disclosure, the crystallization with an ethanol-water system means that the crystallization is performed under a saturated vapor pressure of a specific temperature in the co-presence of ethanol and water.

The concentration mode in step (a-3) is selected in a wide range, as long as the purpose of increasing the solid content of the molecular sieve slurry can be achieved.

It is preferable in the present disclosure that before the concentrating process, step (a-3) further comprises: washing the crystallization mother liquor until the pH of the wash water for washing the crystallization product is below 9.4, preferably below 9.2, for example, the pH is within a range of 8.5-9.2. The present disclosure does not impose specific limitation in regard to the washing process, which may be any of various washing methods conventionally used in the art; in addition, the detergent used in the washing process is not particularly limited in the present disclosure, it may be water, for example. The water may be purified water, deionized water, ion exchange water, chemical water, or other water without containing anions and cations. In the present disclosure, the washing operation may be repeated, and the number of the repeated operation is not particularly defined, the repeated operation may be performed for 1-10 times, for example.

According to a preferred embodiment of the present disclosure, the crystallization mother liquor is washed with water at a temperature of 20-80° C.

According to a preferred embodiment of the present disclosure, the washing and concentration of the molecular sieve is carried out by means of membrane filtration, for example, by using a six-tube membrane. The specific operation is well-known among those skilled in the art, the content will not be repeated here.

According to the method provided by the present disclosure, it is preferable that the method further comprises: the crystallization mother liquor is subjected to ethanol removal prior to the concentrating process (preferably prior to washing, if a washing process is also included in the method) in step (a-3). In the present disclosure, given that the ethanol contains organic oxygen during the industrial production, the discharge of ethanol into wastewater may result in environmental problems, thus the ethanol removal operation is required.

In the present disclosure, the conditions of ethanol removal are selected from a wide range, as long as the purpose of removing ethanol is achieved; the conditions of ethanol removal preferably comprise: the temperature is within a range of 50-90° C., preferably 60-90° C.; the time is within a range of 1-24 h, preferably 1-12 h.

Specifically, the reaction kettle may be opened after the temperature of the reaction kettle is lowered to an operable temperature, and the temperature of the reaction kettle is then raised to 50-90° C. to evaporate the ethanol. In the ethanol removal operation of the present disclosure, water can be added into the reaction kettle to maintain the liquid level of the reaction kettle, which is beneficial to improving efficiency of the ethanol removal process.

In the present disclosure, the solid content of the molecular sieve slurry is selected from a wide range, and preferably, the solid content of the molecular sieve slurry in step (a-3) is within a range of 15-40 wt %, preferably 20-35 wt %. The preferred circumstance is more conducive to improving performance of the prepared catalyst.

According to the present disclosure, the molecular sieve-binder slurry in step (a-4) preferably has a solid content of 10-40 wt %, preferably 10-35 wt %. It is more advantageous to carry out the mist spray forming under the preferred circumstance, such that the abrasion index of the catalyst is lower.

According to the present disclosure, it is preferable in the molecular sieve-binder slurry, the weight ratio of the molecular sieve based on the dry weight relative to the binder calculated by $SiO_2$ is 1:(0.05-1), preferably 1:(0.2-0.8). In the preferable circumstance, the catalyst has better performance, and it is more conducive to improving the conversion rate of cyclohexanone oxime and the selectivity of caprolactam.

The mist spray forming of the present disclosure has the conventional meaning in the art. The conditions of the mist spray forming preferably cause that the particles obtained by the mist spray forming have a particle size of 20-200 μm, further preferably 40-150 μm.

According to the present disclosure, the conditions of the mist spray forming preferably comprise: the inlet temperature is within a range of 180-300° C., preferably 240-260° C.; the outlet temperature is within a range of 80-140° C., and preferably 110-130° C. In the preferred embodiment, the catalyst has better performance, and it is more conducive to improving the conversion rate of cyclohexanone oxime and the selectivity of caprolactam.

In the mist spray forming process, the binder is preferably a precursor of silicon oxide. The present disclosure provides a wide selection range for the precursor of the silicon oxide, as long as the precursor can be converted into the silicon oxide through subsequent roasting. Preferably, the precursor of the silicon oxide is silica sol and/or white carbon black, and further preferably silica sol. The white carbon black of the present disclosure is commercially available. The silica sol may be an acidic silica sol or an alkaline silica sol, and may be commercially available or prepared according to any of the existing technologies. According to the present disclosure, the silica sol preferably has a $SiO_2$ content of 20-45 wt %, preferably 30-40 wt %.

According to the present disclosure, the silica sol may further contain sodium ions, the content of sodium ions is selected from a wide range of the present disclosure, and preferably, the content of sodium ions is not higher than 1,000 μg/g. In the preferred circumstance, it is more conducive to improving performance of the catalyst.

According to the present disclosure, the roasting conditions of step (a-4) preferably comprise: the temperature is within a range of 200-600° C., preferably 250-550° C., and the time is within a range of 1-20 h, preferably 2-18 h.

According to the present disclosure, it is preferable that the roasting may be a multi-stage roasting, and for instance, the roasting may specifically include stage 1) and stage 2); the conditions of the phase 1) comprise: the temperature is within a range of 200-400° C., and the time is within a range of 2-10 h; the conditions of the stage 2) comprise: the temperature is within a range of 400-600° C., and the time is within a range of 2-15 h. Further preferably, the stage 1) includes a stage 1-1) and a stage 1-2), and the conditions of the stage 1-1) include: the temperature is within a range of 200-300° C., the time is within a range of 2-5 h, and the conditions of the stage 1-2) comprise: the temperature is within a range of 300-400° C., and the time is within a range of 2-5 h; the stage 2) comprises a stage 2-1) and a stage 2-2), and the conditions of the stage 2-1) comprise: the temperature is within a range of 400-500° C., the time is within a range of 2-5 h, and the conditions of the stage 2-2) comprise: the temperature is within a range of 500-600° C., and the time is within a range of 8-13 h.

According to a preferred embodiment of the present disclosure, the alkaline buffer solution of a nitrogen-containing compound comprises an ammonium salt and an alkali. The solvent of the alkaline buffer solution of a nitrogen-containing compound is water.

In the present disclosure, the ammonium salt is preferably ammonium nitrate and/or ammonium acetate.

According to the present disclosure, the alkali is preferably at least one selected from the group consisting of ammonia water, tetramethylammonium hydroxide, tetraethylammonium hydroxide, and tetrapropylammonium hydroxide, preferably ammonia water.

According to a preferred embodiment of the present disclosure, the ammonium salt is contained in an amount of 0.1-20 wt %, preferably 0.5-15 wt %; the alkali is contained in an amount of 5-30 wt %, preferably 10-28 wt %.

According to the present disclosure, it is preferable that the alkaline buffer solution of a nitrogen-containing compound has a pH within a range of 8.5-13.5, preferably 10-12, and more preferably 11-11.5.

The present disclosure has wide selection range of the dosage of the alkaline buffer solution of a nitrogen-containing compound, and it is preferable that the alkaline buffer solution of a nitrogen-containing compound is used in an amount of 500-1,500 parts by weight, preferably 700-1,200 parts by weight, relative to 100 parts by weight of the roasted product on a dry basis.

According to the present disclosure, it is preferable that the contacting conditions comprise: the temperature is within a range of 50-120° C., preferably 70-100° C.; the pressure is within a range of 0.5-10 kg/cm$^2$, preferably 1.5-4 kg/cm$^2$; the time is within a range of 0.1-5 h, preferably 1-3 h. In the present disclosure, the contacting process is preferably performed under stirring conditions. The stirring speed is not particularly limited in the present disclosure, and it may be appropriately selected by those skilled in the art according to the actual situation.

According to the method provided by the present disclosure, the contacting process may be subjected to repetitive operation. The number of repetitions is not particularly limited in the present disclosure, it may be determined according to the effect of the contacting process; in order to improve the performance of the catalyst, for example, the contacting process may be may be repeated for 1-3 times.

The present disclosure does not impose specific definition in regard to the conditions for drying the product prepared by contacting the product obtained from the roasting process with the alkaline buffer solution of a nitrogen-containing compound, the drying process may be performed with any means known in the prior art, as long as the solvent is removed, and the drying method includes, but is not limited to, natural drying, heat drying, and forced air drying, and specifically, for example, the drying temperature may be within a range of 100-120° C., and the drying time may be within a range of 2-36 hours.

According to the present disclosure, it is preferable that step (a-5) may further comprise: prior to the drying, sequentially filtering and washing the substances obtained after the roasted product obtained in step (4) is contacted with the alkaline buffer solution of a nitrogen-containing compound. The detergent used in the washing process of the present disclosure is not particularly limited, for example, the detergent may be water. Specifically, the washing process may include: washing until the pH of the filtration clear solution is within a range of 9-10.5.

According to another preferred embodiment of the present disclosure (rotary molding), the catalyst comprises 70-95 wt % of the molecular sieve based on the dry weight and 5-30 wt % of the binder in terms of oxide, based on the dry weight of the catalyst. Further preferably, the preparation method of the catalyst comprises the following steps:

(b-1) mixing ethyl orthosilicate, ethanol, a metal source, tetrapropylammonium hydroxide and water to obtain a colloid mixture; wherein the molar ratio of ethyl orthosilicate calculated by $SiO_2$, ethanol, tetrapropylammonium hydroxide and water is 1:(4-25):(0.06-0.45):(6-100); the weight ratio of the ethyl orthosilicate calculated by $SiO_2$ relative to the metal source calculated by the metal element is (10,000-200,000):1;

(b-2) subjecting the colloid mixture to a two-stage crystallization with an ethanol-hydrothermal system under variable temperatures, wherein the conditions of the two-stage crystallization with an ethanol-hydrothermal system under variable temperatures comprise: crystallizing at 40-80° C. for 0.5-5 days, and crystallizing at 80-130° C. for 0.5-5 days;

(b-3) sequentially filtering and drying the crystallization mother liquor obtained in step (b-2) to obtain a molecular sieve raw powder;

(b-4) crushing the molecular sieve raw powder, blending the crushed molecular sieve raw powder with a binder, and then carrying out rotary molding to obtain spherical particles;

(b-5) roasting the spherical particles, contacting the roasted spherical particles with an alkaline buffer solution containing a nitrogen compound, and subsequently carrying out drying.

Preferred conditions and operations of steps (b-1) and (b-2) according to the present disclosure may be as described above for steps (a-1) and (a-2), respectively, the present disclosure will not provide the unnecessary details here.

The present disclosure does not impose specific definition on the filtering process in step (b-3), it may be performed with various filtration methods conventionally used in the art, as long as the purpose of solid-liquid separation can be achieved.

According to the present disclosure, it is preferable that prior to the filtering process, step (b-3) further comprises: washing the crystallization mother liquor. The washing is not particularly limited in the present disclosure, it may be performed with any of various washing methods conventionally used in the art, and the detergent used in the washing process is not particularly limited in the present disclosure, the detergent may be water, for example. The water may be purified water, deionized water, ion exchange water, chemical water, and other water which does not contain anions and cations.

According to a preferred embodiment of the present disclosure, the crystallization mother liquor is washed with water at 20-80° C., preferably until the pH of the washing liquor is within a range of 7.5-10.

According to a preferred embodiment of the present disclosure, step (b-3) is carried out by washing and filtering the molecular sieve by means of membrane filtration, for example, by using a six-tube membrane.

According to the method provided by the present disclosure, it is preferable that the method further comprises: the crystallization mother liquor is subjected to ethanol removal prior to the filtration (preferably prior to washing, if a washing process is also included in the method) in step (b-3). The specific operation of ethanol removal is as described above and will not be described herein.

According to the method provided by the present disclosure, the conditions of drying in step (b-3) are selected from a wide range, and preferably, the drying conditions may comprise: the drying temperature is within a range of 80-150° C., and the drying time is within a range of 2-36 hours. Further preferably, the drying temperature is within a range of 100-120° C., and the drying time is within a range of 10-30 hours.

According to the present disclosure, it is preferable in step (b-4) that the molecular sieve raw powder is pulverized to 100-1,000 meshes. The preferred circumstance is more conducive to performing the rotary molding. In the present disclosure, the pulverization method is not particularly limited, and the pulverization can be carried out by selecting any conventional technique, specifically, the pulverization is performed on a pulverizer, for example.

The rotary molding of the present disclosure has the conventional meaning in the art. The conditions for rotary molding are preferably such that the particles obtained by rotary molding have a particle diameter of 0.5-3 mm, preferably 0.8-2.5 mm.

According to the present disclosure, the rotary molding in step (b-4) may be performed in the presence or absence of a binder, and preferably, the rotary molding is performed by pulverizing the molecular sieve raw powder and mixing the pulverized molecular sieve raw powder with a binder. The purpose of adding the binder is to make the powder particles adhere to each other during rotation, so as to further enhance strength of the molded product.

According to the present disclosure, it is preferable that in step (b-4), the weight ratio of the molecular sieve based on the dry weight relative to the binder calculated by $SiO_2$ is 1:(0.05-1), preferably 1:(0.1-0.8), more preferably 1:(0.1-0.42). According to the method provided by the present disclosure, the binder is added to ensure that the molecular sieve raw powder is mutually bonded during the rotary process, so as to further increase strength of the catalyst molded product. When the added amount of the binder is insufficient, it is not conducive to forming of the spherical product; when the added amount of the binder is excessive, the spherical product is prone to be soft and sticky, which will influence improvement of the strength.

According to the present disclosure, it is preferable that the rotary molding is carried out in a rotary table molding machine. Specifically, the examples of the present disclosure provide the illustrative description by using a sugar coating machine with a model number BY-1200 purchased from the Tiantai Pharmaceutical Machinery Factory Corporation in Taizhou City, Jiangsu Province of China.

The inventors of the present disclosure have performed in-depth research and comprehension on the operation conditions of the rotary table rolling ball forming through a large number of experiments, the experiments demonstrate that the rotary molding may be influenced by various factors including the residence time, the rotary table inclination angle, the rotary table diameter D, the rotary table depth H, and the rotation speed of the rotary table. In the present disclosure, the residence time refers to the average time from the time when the molecular sieve raw powder is fed into the rotary table molding machine to the time when the molecular sieve raw powder is formed into spherical particles and is separated from the rotary table molding machine, the residence time may be generally within a range of 10-600 minutes, preferably 30-180 minutes. The rotary table inclination angle is an angle between the rotary table and the horizontal line, preferably within a range of 40°-55°, more preferably 45°-50°, it may be, for example, 40°, 45°, 50°, 55°, or an angle between any two of the aforementioned numerical values. When the rotary table inclination angle is less than 40°, it is not favorable to ensure the molding state, and the larger is the inclination angle, the smaller is the diameter of the spherical particles. Preferably, the relationship between the rotary table diameter D and the rotary table depth H is H=0.1-0.3D, preferably H=0.1-0.25D. According to the method provided by the present disclosure, the rotation speed of the rotary table shall be appropriately controlled, if the rotation speed of the rotary table is too high, the forming state is not ideal, the formed product may exhibit a dumbbell shape. Preferably, the rotation speed of the rotary table is within a range of 10-50 rpm, preferably 20-40 rpm.

In the present disclosure, for the sake of obtaining desirable mechanical strength and shape perfectness of the catalyst molded product, it is required to select the appropriate operation process and conditions so as to avoid layering and peeling of product particles. It is preferable that the throughput of the rotary table molding machine may be 20-100 kg/h, preferably 40-80 kg/h, based on the amount of catalyst produced per hour. During the molding process of the rolling balls on the rotary table, the material storage amount can also influence the rotary molding; the material storage amount in the rotary table refers to the amount of micro-ball and pellet catalysts in the rotary table which do not reach the qualified diameter, and the material storage amount is preferably controlled to be ⅒-¼ of the handling capacity.

According to the present disclosure, the rotary molding can also particularly form the material having a particle size which is not within the range of 0.1-3 mm, and the material is called as the rejected material in the present disclosure. The present disclosure does not impose specific limitation in regard to the treatment of the rejected material, for example, the rejected material may be fed into a pulverizer for further crushing, the pulverized material is used as a raw material for the next batch of preparation.

In the rotary molding process, it is preferable that the binder is a precursor of silicon oxide and/or water (preferably deionized water), preferably a precursor of silicon oxide. The details regarding the precursor of silicon oxide are as described above and will not be repeated here.

In step (b-4) of the present disclosure, the pulverized powder sample and the binder may be separately fed into the rotary table molding machine, or the pulverized powder sample and the binder may be uniformly mixed in advance and then fed into the rotary table molding machine.

During the rotary molding process of the present disclosure, the binder may be added at one time or in multiple batches; in order to further improve the mixing uniformity, the binder is preferably added in multiple batches (for example, 2-10 batches). In the present disclosure, the adhesives may be referred to as a first adhesive, a second adhesive, and so on, depending on the number of times of addition. For example, when the binder is added in two batches, the binder is referred to as a first binder and a second binder in sequence. Likewise, in the present disclosure, when the addition of the powder sample is divided into two batches, the molecular sieves are referred to as a first powder sample and a second powder sample in sequence. In the present disclosure, the terms "first" and "second" do not play a limiting role, but to distinguish between operations performed at different stages and the materials added accordingly.

According to a preferred embodiment of the present disclosure, the binder is added in two batches, the binder is divided into a first binder and a second binder sequentially, the powder samples are referred to as a first powder sample and a second powder sample, step (b-4) comprises a step (4-1) and a step (4-2):

step (4-1) comprises the following steps: selecting a first powder sample with the particle size of 100-1,000 meshes from the solid matter obtained from the pulverization, mixing the first powder sample with a first binder, and carrying out a first rotary molding to obtain first particles with a particle size of 0.1-0.8 mm, wherein the mass ratio of the first powder sample relative to the first binder is 1:(0.2-1);

step (4-2) comprises the following steps: selecting a second powder sample with the particle size of 100-1,000 meshes from the solid matter obtained from the pulverization, mixing the second powder sample, a second binder and the first particles, and carrying out a second rotary molding to obtain second particles with a particle size of 1.3-2.5 mm, wherein the mass ratio of the second powder sample relative to the second binder is 1:(0.001-0.5). In the preferred embodiment, the catalyst has a higher crush strength and better catalytic performance.

According to the present disclosure, the first powder sample and the second powder sample in step (4-1) and step (4-2) may adopt the same sieved powder sample or different sieved powder samples. Preferably, the different sieved powder samples. In the preferred circumstance, the product has a higher content of molecular sieve with spherical particles and a higher crush strength. Specifically, for example, the first powder sample has a particle size of 100-1,000 meshes, and the second powder sample has a particle size of 200-800 meshes.

According to the present disclosure, the second powder sample and the second binder in step (4-2) may be separately fed into a rotary disc molding machine, or may be mixed in advance and then fed into the rotary table molding machine. Preferably, the second powder sample is mixed with a second binder, and then pulverized again to 30 mesh or less, and then fed into a rotary disc molding machine having the first particle size described in step (4-1). In the present disclosure, the speed of feeding the molecular sieve and the binder to the rotary disc molding machine is not particularly limited, and specifically, for example, the mixture of the powder sample and the binder may be fed at 20-60 kg per hour.

The present disclosure has a wide selection range of the weight ratio of the first powder sample relative to the second powder sample, the weight ratio may be any proportion according to practical requirements, and it can be adjusted at any time according to the balling condition of the powder samples. Preferably, the weight ratio of the first powder sample relative to the second powder sample is 1:20-100. According to the present disclosure, it is preferable that the first spherical particles have a particle size of 0.05-1.5 mm. According to the present disclosure, the spherical particles preferably have a particle size of 0.8-3 mm.

According to the present disclosure, it is preferable in the present disclosure that the method further comprises drying the molded product after the rotary molding in step (b-4) so as to obtain the spherical particles. The drying process in step (b-4) is not particularly limited in the present disclosure, the drying process may be performed with any conventional technique in the art, as long as the water is removed; the drying method includes, but is not limited to, natural drying, heat drying and forced air drying. The drying temperature may be within a range of 80-200° C., and the drying time may be within a range of 2-24 hours.

According to a preferred embodiment of the present disclosure, after the rotary molding in step (4) (preferably before the drying process), the method further comprises: subjecting the product obtained by rotary molding to a polishing treatment. The adoption of such a preferred embodiment may increase the roundness of the outer surface of the spherical catalyst on the one hand, and further increase the crush strength of the catalyst on the other hand. The polishing treatment may be performed according to the existing technical means in the art. Specifically, for example, the product obtained by rotary molding is blown at 20-50° C. (the moisture can be removed), and the trace amount of water is replenished for many times (e.g., 3-10 times) in the blowing process (the catalyst surface can be moistened, the catalyst is prone to slight and small-range deformation, thereby improving roundness of the balls), and then tightening is carried out (the blowing can be performed for 1-4 hours without replenishing water).

According to the present disclosure, the conditions of roasting in step (b-5) preferably comprise: the temperature is within a range of 200-600° C., preferably 500-580° C.; and the time is 1-20 h, preferably 2-18 h.

According to the present disclosure, the specific operation and conditions for roasting the spherical particles, contacting the roasted spherical particles with alkaline buffer solution of a nitrogen-containing compound, and then drying in step (b-5) are as previously described in step (a-5), the details will not be repeated here.

According to the present disclosure, it is preferable that the method further comprises recovering ethanol from the preparation process of catalyst for providing at least part of the ethanol of step (1) and/or at least part of the ethanol of the crystallization solvent of step (4). By adopting the preferred embodiment, ethanol is used for synthesizing the molecular sieve, so that the selectivity of caprolactam can be further improved; in addition, the ethanol obtained in the synthesis of the molecular sieve can be fully utilized as a solvent for the gas phase Beckmann rearrangement reaction. In the preferred embodiment, the reaction solvent is recycled and the consumption of the reaction solvent is relatively low, thus the ethanol obtained by molecular sieve synthesis can be used for replenishing the consumed part of ethanol as the rearrangement reaction solvent. The ethanol recovered in the synthesis of the molecular sieve may subject to distillation and dehydration and subsequently used as a solvent for gas phase Beckmann rearrangement reaction. Taking a caprolactam production facility with a production capacity of 100,000 ton/year as an example, the production facility consumes 300 tons of ethanol as a reaction solvent and 25-30 tons of catalyst every year. The production of 25-30 tons of catalyst can yield approximately 100-120 tons of ethanol. Therefore, the recovered ethanol is used as a solvent in the gas phase Beckmann rearrangement reaction, such an arrangement not only greatly reduces the production costs (saving about 40% of the solvent cost), but also decrease the discharge amount of pollutants (during the molecular sieve synthesis process in the prior art, when the crystallized slurry is subjected to washing and filtering, the filtrate obtained from the filtering process is directly discharged into water). The inventors of the present disclosure have further discovered that the purpose of improving the selectivity of caprolactam can be achieved by adopting ethanol in the synthesis process of the molecular sieve and using the ethanol as a reaction solvent in the gas phase Beckmann rearrangement reaction. Moreover, when the crude caprolactam is crystallized and refined, a small amount of ethanol is added into a crystallization solvent, the ethanol is conducive for improving the chromaticity and quality of the caprolactam products.

Therefore, it is preferable in the method provided by the present disclosure that the ethanol is used in three core processes, namely molecular sieve synthesis, rearrangement reaction, and crystallization refining, such that the unexpected technical effects are achieved, and the method is more favorable for improving economic benefits.

According to a preferred embodiment of the present disclosure, the ethanol in the crystallization mother liquor of step (a-3) is recovered for providing at least part of the ethanol of step (1) and/or at least part of the ethanol in the crystallization solvent of step (4).

According to another preferred embodiment of the present disclosure, the ethanol in the crystallization mother liquor of step (b-3) is recovered for providing at least part of the ethanol of step (1) and/or at least part of the ethanol in the crystallization solvent of step (4).

According to a preferred embodiment of the present disclosure, the method further comprises dehydrating the ethanol recovered in step (a-3) and/or step (b-3). The dehydration process and the specific applications of the recovered ethanol are described below.

According to the present disclosure, the separation in step (2) is preferably a gas-liquid separation. It is preferable that in step (2), the reaction product obtained in step (1) is subjected to gas-liquid separation to obtain an ethanol solution of the crude caprolactam and a gas phase material flow; the method specifically comprises the following steps: the gas phase Beckmann rearrangement reaction product is subjected to heat exchange and gas-liquid separation to obtain a gas phase material flow (for example, it comprising nitrogen gas, ethanol gas, ammonia gas, water vapor, hydrogen gas, oxygen gas, CO, $CO_2$, gaseous caprolactam (in a trace amount, it pertains to the trace amount of caprolactam entrained in the gas) and a liquid phase material flow (an ethanol solution of crude caprolactam, wherein dozens of various by-products with small amount are contained in different quantities). When methanol is used as the solvent in the gas phase Beckmann rearrangement reaction, the gas phase composition contains a large amount of trimethylamine and dimethyl ether; when the ethanol is used as the solvent, the gas phase composition does not comprise triethylamine and diethyl ether.

According to the present disclosure, the gas phase material flow can be recycled.

According to the present disclosure, the ethanol solution of the crude caprolactam further comprise at least one from the group consisting of acetaldehyde, diethyl ether, acetonitrile, cyclohexene compounds, cyclohexanone, capronitrile compounds, O-ethyl-epsilon-caprolactam imide, cyanopentene compounds, cyclohexenone, cyanocyclopentane, 2-ethoxy-cyclohexanone, cyclohexanol, cyclohexenol, aniline compounds, nitrobenzene compounds, furan, phenol, N-caproamide, N-ethyl-caprolactam, 5,6,7,8-tetrahydronaphthylamine, octahydrophenazine and tetrahydrocarbazole.

According to the present disclosure, it is preferable that an ethanol solution of crude caprolactam is subjected to distillation to obtain the ethanol and crude caprolactam. The distillation can be performed in an ethanol solvent recovery tower, and the operating conditions of the ethanol solvent recovery tower can be selected from a wide range of the present disclosure, for example, the distillation is preferably carried out at 340-360 kPa (absolute pressure), the feedstock temperature is within a range of 50-60° C., the tower top temperature is within a range of 110-115° C., the tower top pressure (absolute pressure) is within a range of 340-360 kPa, the tower kettle temperature is within a range of 130-140° C., and the tower kettle pressure (absolute pressure) is within a range of 340-360 kPa, the water content of the tower kettle is within a range of 0.5-1.5 wt %, and the tower kettle obtains crude caprolactam containing light and heavy impurities, and the ethanol (an aqueous ethanol gas phase material flow) is obtained from the tower top. The aqueous ethanol gas phase material flow obtained at the tower top may be subjected to dehydrating by a set of molecular sieve adsorption dehydration device (the molecular sieve adsorption dehydration is an endothermic process, the temperature is preferably higher than that of the aqueous ethanol gas phase material flow, and the temperature of the molecular sieve adsorption dehydration device is further preferably within a range of 130-140° C.).

The dehydration is performed to obtain an anhydrous ethanol (with water content less than 5,000 ppm, preferably less than 2,000 ppm, more preferably lower than 500 ppm).

According to a preferred embodiment of the present disclosure, the ethanol solvent recovery tower is followed by an ethanol dehydration tower to remove a substantial portion of the water from the aqueous ethanol gas phase material flow, and then subjected to the above-described dehydration (molecular sieve adsorption dehydration). The energy consumption can be further reduced by adopting the method. The present disclosure has wider selection range for the ethanol dehydration tower, and it is preferable that the feedstock temperature is within a range of 130-140° C., the tower top temperature is within a range of 22-28° C., the tower top pressure is within a range of 8-9 kPa, the tower kettle temperature is within a range of 135-140° C., the tower kettle pressure is within a range of 8-12 kPa, and the water content of the tower kettle is within a range of 0.1-1 wt %.

According to the present disclosure, the anhydrous ethanol is preferably obtained by the pervaporation separation technology of a NaA molecular sieve membrane material. The NaA molecular sieve membrane material has a pore diameter of 0.42 nm, and exhibits the characteristics such as strong hydrophilic property, high separation selectivity and robust thermochemical stability, so that the NaA molecular sieve membrane material is selected to separate a small amount of water in ethanol, as compared with an azeotropic distillation technology, an application of the pervaporation separation technology for dehydrating the ethanol can save the energy consumption by more than 50%, allow the equipment to save more than ⅘ space, and the discharge amount of the three wastes (i.e., waste gas, waste water and waste residues) is significantly reduced. The diffusion rates of components in the aqueous ethanol gas phase material flow are different when the components pass through the membrane, the component having a high diffusion rate may pass through the membrane first, while the component having a low diffusion rate can hardly or does not pass through the membrane, so as to fulfill the purpose of separating the components. Water can be separated by rapidly passing through the NaA molecular sieve membrane material.

According to the present disclosure, the ethanol and/or anhydrous ethanol obtained in step (2) is preferably used for providing at least part of the ethanol in step (1) and/or at least part of the ethanol in the crystallization solvent in step (4).

The present disclosure has a relatively low quality requirement on the ethanol used in the molecular sieve synthesis process, for example, the ethanol may be the ethanol aqueous solution having an ethanol content more than 95 wt %; however, the present disclosure has a relatively high quality requirement on the ethanol used in the gas phase Beckmann rearrangement reaction of cyclohexanone oxime in step (1), the ethanol is preferably anhydrous ethanol having a water content less than 2,000 ppm. The present disclosure has the highest quality requirement on the ethanol used in the crystallization process, the water content of the ethanol used in the crystallization in step (4) is preferably less than 200 ppm. Those skilled in the art can apply ethanol to at least one of the preparation of molecular sieves, the gas phase Beckmann rearrangement reaction of cyclohexanone oxime, and the crystallization process according to the actual condition of recovered ethanol.

According to the present disclosure, it is preferable that in step (3), impurities with a boiling point lower than that of caprolactam in the crude caprolactam are removed by vacuum distillation. Specifically, the crude caprolactam is sent to a light component removal tower to remove impurities with a boiling point lower than that of caprolactam (removed from the tower top); the material retained in the tower kettle is crude caprolactam following removal of light impurities (i.e., light component removal product, it still contains impurities with boiling points higher than that of caprolactam), and the light component removal product is conveyed to a crystallization refining unit for performing crystallization. An use of the preferred embodiment can avoid the problems in the prior art brought by removing impurities with a boiling point higher than that of caprolactam by distillation. Distillation in the process of removing heavy component needs to be carried out under low vacuum and high temperature, the distillation for a long-time may cause degrading of the caprolactam quality and an occurrence of polymerization, the impurities per se may carry out reaction, and the impurities may further react with caprolactam, such that more impurities are generated, and the content of heavy impurities is increased. The caprolactam containing a large amount of heavy impurities at the distillation kettle bottom needs to be discharged outside, and the yield of caprolactam is seriously affected. The aforementioned problems not only increase the operating costs, but also cause a decreased yield of the caprolactam and a declined product quality, resulting in the decreased economic efficiency of the overall process.

The specific operation of the vacuum distillation in the present disclosure is not particularly limited, and it can be performed with a conventional method in the art. The conditions of the light component removal tower comprise: the feedstock temperature is within a range of 135-140° C., the tower top temperature is within a range of 77-83° C., the tower top pressure is within a range of 0.8-1.2 kPa, the tower kettle temperature is within a range of 145-150° C., the tower kettle pressure is within a range of 1-3 kPa, and the water content in the tower kettle is zero.

According to the present disclosure, the light component removal product is directly subjected to crystallization, and the present disclosure does not comprise a process for removing impurities with a boiling point higher than that of caprolactam through distillation.

It is understandable for those skilled in the art that the removal of impurities having a boiling point lower than that of caprolactam means that the impurities having a boiling point lower than that of caprolactam are removed by distillation as far as possible under the conditions below the boiling point of caprolactam, it does not exclude the circumstances that a small amount of impurities having a boiling point lower than that of caprolactam residues in the light component removal product, and a small amount of impurities having a boiling point higher than that of caprolactam is entrained and removed by the distillation.

According to the present disclosure, preferably, the used amount of the crystallization solvent in step (4) is 150-400 parts by weight, preferably 200-300 parts by weight, relative to 100 parts by weight of the light component removal product.

Preferably, the crystallization temperature is within a range of 10-65° C., preferably 15-55° C., more preferably 20-45° C. The crystallization of the present disclosure may be cooling crystallization, evaporative crystallization or vacuum adiabatic cooling crystallization, preferably evaporative crystallization. The crystallizer can be selected from a wide range of crystallizers, such as a cooling crystallizer, an evaporative crystallizer, or a vacuum crystallizer.

According to the present disclosure, the crystallization solvent preferably comprises ethanol, a solvent A and optionally a solvent B; the solubility of caprolactam in the solvent A and solvent B is less than 5 wt % at 20° C., and the solubility of caprolactam in the solvent A is larger than the solubility of caprolactam in the solvent B.

The content of ethanol in the crystallization solvent is preferably within a range of 0.5-2 wt %, and more preferably within a range of 0.5-1.5 wt %. The inventors of the present disclosure have discovered in the research process that the temperature for crystal precipitation can be increased by adding a small amount of ethanol into the crystallization solvent, so as to ensure that an oil precipitation phenomenon does not occur during the second crystallization and the third crystallization of the mother liquor, the scab on the inner wall of the crystallization kettle and the stirring paddle is delayed or even inhibited, the chromaticity of caprolactam crystals is improved, it is conducive to improving the quality and yield of caprolactam products.

According to the present disclosure, the solvent A is preferably selected from ethers having 2-8 carbon atoms; further preferably, the solvent A is one selected from the group consisting of methyl ethyl ether, diethyl ether, n-propyl ether, isopropyl ether, n-butyl ether, ethylene glycol dimethyl ether, vinyl ether, methyl tert-butyl ether and ethyl tert-butyl ether.

According to the present disclosure, the solvent B is preferably selected from alkanes having 6-12 carbon atoms; further preferably, the solvent B is at least one selected from the group consisting of n-hexane, n-heptane, n-octane, n-nonane, methylhexane, isohexane, neohexane, cyclohexane, methylcyclopentane, methylcyclohexane, isoheptane, isooctane and isononane.

According to the present disclosure, it is preferable that the number of carbon atoms of the solvent A is less than that of the solvent B.

According to a most preferred embodiment of the present disclosure, the solvent A is isopropyl ether and the solvent B is n-heptane. The solubility of caprolactam in isopropyl ether is 4.15 wt % (under the condition of 20° C.); the solubility of caprolactam in n-heptane is lower than 2.0 wt % (under the condition of 20° C.). The isopropyl ether is particularly suitable to be used as a crystallization solvent of caprolactam, especially suitable to be applied in an evaporative crystallization process, because the isopropyl ether has a low boiling point, it can be easily recovered and reused as a crystallization solvent (only through vacuumizing), the quality of caprolactam products is desirable, the solubility of caprolactam in n-heptane is particularly low, so that the crystallization yield is particularly high, in addition, the solubility of impurities in n-heptane is also particularly low, so that the impurity removal capability of n-heptanes obviously not as strong as that of isopropyl ether. Since the solubility of caprolactam in n-heptane is very low, an oil precipitation phenomenon will occur during mother liquor crystallization (the second crystallization or third crystallization) (if the proportion of n-heptane in the mainline crystallization (first crystallization) is greater than 50 wt %, the oil precipitation phenomenon is also easy to occur in the mainline crystallization (first crystallization)), which seriously affects the overall quality of caprolactam, and basically, n-heptane cannot be used alone as a crystallization solvent, the addition of ethanol is extremely conducive to improving product quality of caprolactam, in particular, significantly improving chromaticity of caprolactam. The addition of the ethanol enables the crystallization temperature to be increased when the mother liquor is subjected to the first recrystallization and the second recrystallization, and the phenomenon of oil precipitation is inhibited and delayed. The occurrence of oil precipitation phenomenon means that the product quality of caprolactam is seriously affected; if recrystallization is performed after an occurrence of the oil precipitation phenomenon, a large amount of impurities are enriched and concentrated on caprolactam crystals. The preferred embodiment is more favorable for inhibiting the occurrence of the oil precipitation phenomenon, slowing down the phenomenon of scabbing and scaling in the crystallization process and further improving the quality and the yield of caprolactam products.

According to a preferred embodiment of the present disclosure, the solvent B is contained in the crystallization solvent in an amount of 0-48 wt %, preferably 1-35 wt %. The preferred embodiment is more advantageous to exert the synergistic effect of ethanol, the solvent A and the solvent B.

According to the method provided by the present disclosure, a seed crystal may be added or not added during the crystallization process, which is not limited by the present disclosure. According to the method of the present disclosure, one or more crystallizations may be performed, the present disclosure does not impose specific limitation thereto, it can be appropriately selected by those skilled in the art according to the practical conditions. In order to further improve purity of the product, the method provided by the present disclosure preferably comprises multiple crystallizations, such as the second crystallization.

According to the present disclosure, it is preferable that the method further comprises subjecting the material obtained by crystallization to a solid-liquid separation. The solid-liquid separation may be centrifugal separation; the device for carrying out the solid-liquid separation may be selected from a wide range, for example, a continuous scraper centrifugal filter, a centrifugal separation type decanter, a countercurrent washing apparatus and the like, and preferably a pressure filter, which has washing and separating functions and can reduce the used amount of washing solvent. The device has the dual functions of separation and washing, both the caprolactam crystal and the crystallization mother liquor are obtained through the solid-liquid separation.

According to the present disclosure, preferably the crystallization comprises: the caprolactam crystals obtained by the solid-liquid separation are subjected to washing (preferably, the washing solvent is the same as the above-mentioned crystallization solvent). When the crystallization is a second crystallization, the crystallization further comprises: subjecting the solid phase obtained by washing to a second evaporative crystallization. The selection range of the kind and amount of the solvent for the second evaporative crystallization may be the same as or different from those for the primary crystallization, and the present disclosure does not impose special limitation thereto, those skilled in the art can select the solvent appropriately according to the practical condition.

In order to further improve the product yield, it is preferable that the method further comprises subjecting the crystallization mother liquor to a second evaporative crystallization, and then carrying out a solid-liquid separation. Specifically, the crystal obtained from the second evaporative crystallization can be mixed with the light component removal product in step (4), and the mixture is used as a raw material for the first crystallization. If the yield of caprolactam is not ideal, the mother liquor obtained by the solid-liquid separation after the second crystallization can be subsequently subjected to the third crystallization, such that the yield of caprolactam can be further ensured.

According to a preferred embodiment of the present disclosure, the method further comprises recovering the crystallization solvent of the second crystallization and/or the third crystallization, and continuing to use it as the first crystallization solvent.

According to the present disclosure, preferably, the hydrogenation reaction of step (5) is performed in the presence of water and a hydrogenation catalyst.

The hydrogenation catalyst is preferably at least one selected from the group consisting of a nickel-based catalyst, a palladium-based catalyst and a platinum-based catalyst, preferably a nickel-based catalyst, which may be, for example, a commercially available Raney Ni catalyst; the hydrogenation catalyst may be commercially available or prepared by itself, the present disclosure does not impose specific limitation thereto.

According to the present disclosure, it is preferable that the crystalline crystal accounts for 60-90 wt %, preferably 75-85 wt %, of the total amount of crystalline crystals and water during the hydrogenation reaction process. The preferred embodiment has low energy consumption and small discharge amount of wastewater.

The present disclosure has wide selection range in regard to the conditions of the hydrogenation reaction, and the conditions of the hydrogenation reaction preferably comprise: the temperature is within a range of 50-150° C.; the pressure is within a range of 0.2-1.5 MPa, the ratio of a molar weight of caprolactam relative the molar weight of hydrogen is within a range of 0.001-0.5, preferably 0.01-0.25. The unreacted hydrogen can be further recycled. The pressure refers to an absolute pressure.

According to the method of the present disclosure, the reactor for carrying out the hydrogenation reaction is not particularly limited, it may be a magnetically stabilized bed reactor, a fixed bed reactor or a slurry bed kettle type reactor; the fixed bed reactor may be selected for the hydrogenation reaction of impurities in caprolactam in the presence of an organic solvent. Slurry bed kettle type reactors (more preferably with stirring paddles) are preferred in the present disclosure.

In an embodiment of the present disclosure, the method provided herein further comprises collecting the caprolactam product by evaporation (distilling water under an atmospheric pressure) and/or vacuum distillation (distilling caprolactam, for example, distillation under reduced pressure of 1-3 kPa) process after the hydrogenation reaction, so as to obtain a caprolactam product having a high absorption of potassium permanganate, a lower volatile base value, and an extinction value.

The present disclosure will be described in detail below with reference to examples.

Unless otherwise specified in the following examples, the room temperature refers to 25° C.;

The content of the metal elements was measured by using an inductively coupled plasma (ICP) atomic emission spectrometer 7000DV, manufactured by PE (Perkin Elmer Incorporation) of the USA, under the test conditions as follows: the molecular sieve was dissolved by using HF acid to completely dissolve silicon oxide and metal oxide in the sample, and the content of metal ions was measured in the aqueous solution.

The external specific surface area and BET specific surface area of the molecular sieve were measured by an automatic adsorption apparatus with a model number Micromeritics ASAP-2460 manufactured in the USA, under the following test conditions: $N_2$ was used as an adsorbate, the adsorption temperature was −196.15° C. (liquid nitrogen temperature), and degassing was performed at 1.3 Pa and the constant temperature 300° C. for 6 hours.

The X-ray diffraction spectrum was recorded by a Miniflex600 type diffractometer manufactured by the Rigaku Corporation in Japan, and the test conditions were as follows: Cu target Kα radiation, Ni optical filter, the tube voltage was 40 kV, the tube current was 40 mA;

The prepared sample was analyzed by a field emission scanning electron microscope with a model number S-4800 manufactured by the Hitachi Corporation of Japan;

The particle size and particle size distribution of the catalyst obtained by the mist spray forming were measured by a 2000E type laser particle size analyzer manufactured by the Dandong Bettersize Instruments Co., Ltd., the test method was a wet process test, water was used as a medium, and the mass concentration of a sample was within a range of 0.5%-2%, the scanning speed was 2,000 times/second;

The mist spray forming was carried out in a mist spray forming apparatus with a model number LT-300 manufactured by the Wuxi Tianyang Spray Drying Equipment Co., Ltd.;

The rotary table molding machine was a sugar coating machine with a model number BY-1200, manufactured by the Tiantai Pharmaceutical Machinery Factory Corporation in Taizhou City, Jiangsu Province of China.

The following test methods were used in the following examples to evaluate the relevant parameters of the prepared caprolactam crystals and caprolactam product:

(1) Purity of Caprolactam

The purity of caprolactam was measured by gas chromatography, wherein the gas chromatograph was the gas chromatograph with a model number 7890B manufactured by the Agilent Technologies Inc., with a hydrogen flame ion detector and a PEG20M capillary chromatographic column, the column length was 60 m, the vaporization chamber temperature was 250° C., the detection chamber temperature was 240° C., the column temperature was subjected to the programmed temperature rise, the constant temperature 110° C. was kept for 8 minutes, the temperature was raised to 230° C. at a heating rate of 15° C./min and then kept constant for 14 minutes, and the lowest detection limit of the chromatogram was 0.1 µg/g.

(2) Potassium Permanganate Value (PM Value) of Caprolactam

The potassium permanganate value of caprolactam can be measured by visual comparison with a standard solution, which is composed of 3 g Co(NO3)2·6H2O and 0.012 g K2Cr2O7 in 1 L of water. One milliliter of 0.01 mol/L potassium permanganate solution is added to 100 mL of 3 wt % aqueous caprolactam solution at 20° C. The time (s) taken for the color to change to that of the standard solution is referred to as the potassium permanganate value.

(3) Volatile Basicity (VB)

In alkaline medium, the alkaline low molecular impurities in the sample were distilled out, and absorbed by a known amount of hydrochloric acid solution, and the excess hydrochloric acid was back-dripped with sodium hydroxide standard solution. The molar number of the acid consumption per kilogram of sample was taken as the measured value of the volatile base. The calculation formula was as follows:

VB (mmol/kg)=[($V_0$-V)×$C_{NaOH}$/M]×1000

In the formula: $V_0$ was the volume of NaOH standard solution consumed in the blank test, and the unit was mL;

V was the volume of NaOH standard solution consumed by the sample, and the unit was mL;

$C_{NaOH}$ was the accurate concentration of NaOH standard solution, and the unit was mol/L;

M was the sample mass in the unit of gram (g).

(4) Extinction Value E (at 290 nm Wavelength)

50 g of caprolactam was weighed and placed in a 300 ml Erlenmeyer flask, 50 ml of distilled water was added, shaken to completely dissolve the sample, and allowed to stand for 10 minutes. Using a spectrophotometer, at a wavelength of 290 nm, the extinction value of the sample with a concentration of 50% relative to distilled water was detected.

(5) Chromatic Value

Caprolactam (50 g) was weighed and placed in a 300 ml Erlenmeyer flask, 50 ml of distilled water was added, shaken to completely dissolve the sample, and allowed to stand for 10 minutes. Then a light absorbance value through the solution of UV ray having a wavelength of 390 nm was measured using water as a reference solution, respectively.

(6) Acidity and Alkalinity

The caprolactam was dissolved in water, methyl red-methylene blue was used as an indicator, the free acid or free base in the sample was titrated by using the hydrochloric acid or sodium hydroxide standard solution. The calculation formula was as follows:

Acidity (mmol/kg)=(V×$C_{HCl}$)/M×1000

Alkalinity (mmol/kg)=(V×$C_{NaOH}$)/M×1000

In the formula: V was the volume of the standard solution consumed by the sample, the unit was mL;

$C_{HCl}$ was the accurate concentration of HCl standard solution, the unit was mol/L;

$C_{NaOH}$ was the accurate concentration of NaOH standard solution, the unit was mol/L;

M is the sample mass in the unit of gram (g).

The following preparation examples were used for illustrating the preparation method of the catalyst of the present disclosure.

Preparation Example 1 (Mist Spray Molding)

(1) 290 kg of ethanol with a content of 95 wt % and 198.5 kg of tetrapropylammonium hydroxide aqueous solution with a content of 22.5 wt % were respectively added into a 2 m³ stainless steel reaction kettle, and subjected to stirring, 208 kg of ethyl orthosilicate was further added, the mixture was stirred for 30 minutes, 280 kg of water and 348 g of Al(NO3)3·9H2O were subsequently added, the mixture was subjected to continuous agitation at room temperature for 4 hours to form a colloid mixture, wherein the molar ratio of ethyl orthosilicate calculated by $SiO_2$:ethanol:tetrapropylammonium hydroxide:water was 1:10:0.22:25; the weight ratio of ethyl orthosilicate calculated by $SiO_2$ relative to metal source calculated by metal elements was 23500:1.

(2) The colloid mixture was initially subjected to crystallizing in an ethanol-hydrothermal system at 70° C. for 1 day, and then subjected to crystallizing in the ethanol-hydrothermal system at 100° C. for 2 days, the colloid mixture was cooled, the kettle cover was opened, the pH of the crystallization mother liquor was 13.85.

(3) The obtained crystallization mother liquor was subjected to an ethanol removal treatment at the temperature of 80° C. for 6 hours, water was continuously supplemented during the treatment process, the materials were maintained at a certain liquid level, an aqueous ethanol gas phase material flow was recovered for later use, 510 kg of ethanol aqueous solution (with the ethanol content 88 wt %) was received by an ethanol recovery tank (which was provided with cooling water for cooling down), a part (290 kg×0.95÷0.88=313 kg) of the recovered ethanol aqueous solution was recycled in the synthesis process of the molecular sieve in step (1), the remaining part of the ethanol aqueous solution was conveyed for carrying out azeotropic distillation to obtain ethanol with a content of 95 wt %, the ethanol was then subjected to molecular sieve adsorption dehydration to obtain anhydrous ethanol with the water content less than 2,000 ppm, the anhydrous ethanol was used as ethanol for the gas phase Beckmann rearrangement reaction.

The product obtained by the ethanol removing treatment was subjected to a membrane filtration with a 50 nm six-tube membrane, and then subjected to washing with water at the temperature of 40-60° C. and the used amount of 13 m³, and the pH value of the washing water for the crystallization product reached 9.0. The slurry obtained after washing was concentrated to obtain 270 kg of molecular sieve slurry having a solid content of 20.7 wt %.

A small amount of the molecular sieve slurry was taken and subjected to drying at 120° C. for 20 hours, the molecular sieve slurry was then subjected to roasting at 550° C. for 6 hours to produce the molecular sieve, wherein the molecular sieve had a content of metal elements of 41.2 µg/g, the BET specific surface area of 436 m²/g, and the external specific surface area of 45 m²/g;

The molecular sieve was subjected to an X-ray diffraction (XRD) spectrum analysis, the XRD spectrum of the molecular sieve had the characteristics consistent with those of the MFI structure standard XRD spectrum illustrated on the literature *Micropore Materials*, Vol. 22, p 637, 1998, it demonstrated that the molecular sieve had the MFI crystal structure;

The molecular sieve was analyzed by a transmission electron microscope (TEM), the analysis results illustrated that the molecular sieve with a topological structure exhibited uniform crystal grain particle size, the particle size was within a range of 0.15-0.2 µm.

(4) The part of the molecular sieve slurry obtained in step (3) was mixed with 33 kg of alkaline silica sol with the content of 30 wt % (the pH value was 9.5, the content of sodium ions was 324 ppm, the content of $SiO_2$ was 40 wt %, and the surface area of $SiO_2$ obtained after roasting was 225 m$^2$/g), wherein the weight ratio of the molecular sieve based on the dry weight in the molecular sieve slurry relative to the alkaline silica sol calculated by $SiO_2$ was 1:0.175, the mixture was stirred uniformly and pulped to obtain molecular sieve-binder mixed slurry with the solid content of 22 wt %. The molecular sieve-binder mixed slurry was conveyed to a mist spray forming device for performing the mist spray forming, wherein the inlet temperature and the outlet temperature were 250° C. and 120° C. respectively. The mixture was then fed into a 3 m$^3$ heating shuttle furnace, was subjected to roasting at 280° C., 400° C. and 480° C. for 2 h respectively, and was finally subjected to roasting at 550° C. for 12 h to obtain 64 kg microsphere molecular sieve, wherein the content of the all-silicon molecular sieve containing a trace amount of aluminum ions was 85 wt %, and the content of the binder calculated by $SiO_2$ was 15 wt %.

100 kg of the microsphere molecular sieve and 1,000 kg of an alkaline buffer solution of a nitrogen-containing compound (the alkaline buffer solution of a nitrogen-containing compound was a mixed solution of ammonia water and an ammonium nitrate aqueous solution, wherein the content of the ammonia water was 26 wt %, the content of the ammonium nitrate in the ammonium nitrate aqueous solution was 7.5 wt %, the weight ratio of the ammonia water relative to the ammonium nitrate aqueous solution was 3:2, and the pH value was 11.35) were added into a 2 m$^3$ stainless steel reaction kettle, the mixture was subjected to stirring at a temperature of 85° C. and under the pressure of 2.6 kg/cm$^2$ for 1.5 hours, then subjected to filtering, and drying at 120° C. for 24 hours, the contact operation of the alkaline buffer solution of a nitrogen-containing compound was then repeated once under the same conditions, subjected to filtering, and washing until the pH of a filtration clear solution was 9, and subsequently subjected to drying at 120° C. for 24 hours to prepare the microsphere molecular sieve catalyst S-1. The measurement result showed that the particle size of the microsphere molecular sieve catalyst was concentrated within a range of 20-150 μm.

Preparation Example 2 (Rotary Molding)

(1) 482 kg of ethanol with a content of 95 wt % and 302 kg of tetrapropylammonium hydroxide aqueous solution with a content of 22.5 wt % were respectively added into a 2 m$^3$ stainless steel reaction kettle, and subjected to stirring, 347 kg of ethyl orthosilicate was further added, the mixture was stirred for 30 minutes, 332 kg of water and 38.65 g of Fe(NO$_3$)$_3$.9H$_2$O were subsequently added, the mixture was subjected to continuous agitation at room temperature for 4 hours to form a colloid mixture, wherein the molar ratio of ethyl orthosilicate calculated by $SiO_2$:ethanol:tetrapropylammonium hydroxide:water was 1:10:0.2:20; the weight ratio of ethyl orthosilicate calculated by $SiO_2$ relative to metal source calculated by metal elements was 18666:1.

(2) The colloid mixture was initially subjected to crystallizing in an ethanol-hydrothermal system at 70° C. for 1 day, and then subjected to crystallizing in the ethanol-hydrothermal system at 100° C. for 2 days, so as to obtain crystallization mother liquor.

(3) The obtained crystallization mother liquor was subjected to an ethanol removal treatment at the temperature of 85° C. for 10 hours, water was continuously supplemented during the treatment process, the materials were maintained at a certain liquid level, an aqueous ethanol gas phase material flow was recovered for later use, the recovering process of ethanol was same as the Preparation Example 1; the product obtained by ethanol removing treatment was then subjected to washing and filtering in sequence, and drying at 120° C. for 24 hours to obtain about 135.5 kg of molecular sieve raw powder;

A suitable amount of the molecular sieve raw powder was taken and subjected to roasting at 550° C. for 6 hours to obtain a molecular sieve sample, wherein the content of metal elements was 49.4 ppm, the BET specific surface area was 426 m$^2$/g, the external specific surface area was 44 m$^2$/g; the XRD spectrum of the molecular sieve product had the characteristics consistent with those of the MFI structure standard XRD spectrum illustrated on the literature *Micropore Materials*, Vol. 22, p 63'7, 1998, it demonstrated that the molecular sieve had the MFI crystal structure;

As can be seen from the scanning electron microscope picture, the molecular sieve with a MFI topological structure exhibited uniform crystal grain particle size, the particle size was within a range of 0.1-0.2 μm.

(4) The molecular sieve raw powder was pulverized, 2 kg of molecular sieve raw powder was sieved into the molecular sieve power sample with 100-1,000 meshes, the molecular sieve power sample was placed in a rotary table molding machine, the rotary table molding machine (a sugar coating machine with a model number BY-1200 manufactured by the Tiantai Pharmaceutical Machinery Factory Corporation in Taizhou City, Jiangsu Province of China) had a rotary table diameter of 1.2 m, a rotary table depth of 450 mm, a rotary table inclination angle was determined to be 50°, and the rotation speed of the rotary table was set to be 30 rpm. 1.5 kg of deionized water was sprayed into the rotary table molding machine to obtain the first spherical particles having a particle size of about 0.2-0.8 mm;

In addition, 110 kg of powder sample sieved into 200-800 meshes and 50 kg of alkaline silica sol (the content of sodium ions was 543 ppm, the content of $SiO_2$ was 30 wt %) were mixed according to the weight ratio of 2.2:1, and subjected to crushing again, the particles with the particle size less than 30 meshes was taken, 160 kg of the particles was added at a constant speed into the rotary table molding machine with the first spherical particles, the adding process was performed within 240 min; then subjected to sieving with 12 meshes and 9 meshes sieves to obtain about 100 kg of spherical particles with a particle size of 1.5-2 mm;

(5) 100 kg of the obtained spherical particles was subjected to blowing at 45° C., trace amount of water was replenished into the spherical particles for many times during the process, then subjected to tightening for 2 hours, and drying at 120° C. for 24 hours, and roasting at 550° C. for 10 hours to obtain 72 kg of a roasted product with the molecular sieve content of 86%;

45 kg of the roasted product and 450 kg of an alkaline buffer solution (the alkaline buffer solution was a mixed solution of ammonia water and an ammonium nitrate aqueous solution, wherein the content of the ammonia water was 26 wt %, the content of the ammonium nitrate in the ammonium nitrate aqueous solution was 7.5 wt %, the weight ratio of the ammonia water relative to the ammonium nitrate aqueous solution was 3:2, and the pH value was 11.35) was added into a 1 m$^3$ pressure reaction kettle, the mixture was subjected to stirring at a temperature of 82° C. and under the pressure of 2.3 kg/cm$^2$ for 1.5 hours, then subjected to washing, filtering and drying to prepare the microsphere molecular sieve catalyst S-2.

The particle size of the catalyst was within a range of 1.4-1.8 mm, and the crushing strength was 28N per particle.

Preparation Example 3 (Mist Spray Molding)

(1) 725 kg of ethanol with a content of 95 wt % and 302 kg of tetrapropylammonium hydroxide aqueous solution with a content of 22.5 wt % were respectively added into a 2 m$^3$ stainless steel reaction kettle, and subjected to stirring, 347 kg of ethyl orthosilicate was further added, the mixture was continuously stirred, 330 kg of water and 37.37 g of Cr(NO$_3$)$_3$.9H$_2$O were subsequently added, the mixture was subjected to continuous agitation at room temperature for 4 hours to form a colloid mixture, wherein the molar ratio of ethyl orthosilicate calculated by SiO$_2$:ethanol:tetrapropylammonium hydroxide:water was 1:13:0.2:20; the weight ratio of ethyl orthosilicate calculated by SiO$_2$ relative to metal source calculated by metal elements was 20600:

(2) The colloid mixture was subjected to crystallizing in an ethanol-hydrothermal system, wherein the crystallization conditions comprise: initially subjected to crystallizing at 65° C. for 1 day, and then subjected to crystallizing at 120° C. for 2 days, so as to obtain the crystallization mother liquor with a pH of 13.54.

(3) The obtained crystallization mother liquor was subjected to an ethanol removal treatment at the temperature of 85° C. for 10 hours, water was continuously supplemented during the treatment process, the materials were maintained at a certain liquid level, an aqueous ethanol gas phase material flow was recovered for later use, the recovering process of ethanol was same as the Preparation Example 1; the product obtained by ethanol removing treatment was then subjected to washing and concentrating by using a 50 nm six-tube membrane, and subjected to washing with water at the temperature of 40-60° C., wherein the used amount of the washing water was 6.5 m$^3$, and the pH value of the washing water for the crystallization product reached 9.0. 375 kg of molecular sieve slurry with the solid content of 28.4 wt % was obtained after the washing and concentration process;

A small amount of the molecular sieve slurry was taken and subjected to drying at 120° C. for 20 hours, the molecular sieve slurry was then subjected to roasting at 550° C. for 6 hours to produce the molecular sieve, wherein the molecular sieve had a content of metal elements of 46.8 μg/g, the BET specific surface area of 435 m$^2$/g, and the external specific surface area of 46 m$^2$/g;

The X-ray diffraction (XRD) spectrum of the molecular sieve had the characteristics consistent with those of the MFI structure standard XRD spectrum illustrated on the literature *Micropore Materials*, Vol. 22, p 637, 1998, it demonstrated that the molecular sieve had the MFI crystal structure;

The transmission electron microscope (TEM) photo showed that the molecular sieve with a MFI topological structure exhibited uniform crystal grain particle size, the particle size was within a range of 0.1-0.2 μm;

(4) The part of the molecular sieve slurry obtained in step (3) was mixed with 96 kg of alkaline silica sol with the content of 30 wt % (the pH value was 9.5, the content of sodium ions was 324 ppm, the content of SiO$_2$ was 40 wt %, and the surface area of SiO$_2$ obtained after roasting was 225 m$^2$/g), wherein the weight ratio of the molecular sieve based on the dry weight in the molecular sieve slurry relative to the alkaline silica sol calculated by SiO$_2$ was 76:24; 330 kg of water was further added, the mixture was stirred uniformly and pulped to obtain molecular sieve-binder mixed slurry with the solid content of 15 wt %. The molecular sieve-binder mixed slurry was conveyed to a mist spray forming device for performing the mist spray forming, wherein the inlet temperature and the outlet temperature were 260° C. and 125° C. respectively. The mixture was then fed into a 3 m$^3$ heating shuttle furnace, was subjected to roasting at 280° C., 400° C. and 480° C. for 2 h respectively, and was finally subjected to roasting at 550° C. for 12 h to obtain 119.8 kg microsphere molecular sieve, wherein the content of the silicon molecular sieve having a MFI topological structure and containing metal ions with extremely trace Lewis acid characteristic was 76 wt %, and the content of the binder calculated by SiO$_2$ was 24 wt %;

100 kg of the microsphere molecular sieve and 1,000 kg of an alkaline buffer solution of a nitrogen-containing compound (the alkaline buffer solution of a nitrogen-containing compound was a mixed solution of ammonia water and an ammonium nitrate aqueous solution, wherein the pH value was 11.35, the content of the ammonia water was 26 wt %, the content of the ammonium nitrate in the ammonium nitrate aqueous solution was 7.5 wt %, the weight ratio of the ammonia water relative to the ammonium nitrate aqueous solution was 3:2) were added into a 2 m$^3$ stainless steel reaction kettle, the mixture was subjected to stirring at a constant temperature of 90° C. and under the pressure of 3.2 kg/cm' for 2 hours, then subjected to filtering, and drying at 90° C. for 12 hours, the contact operation of the alkaline buffer solution of a nitrogen-containing compound was then repeated once under the same conditions, subjected to filtering, and washing until the pH of a filtration clear solution was about 9, and subsequently subjected to drying at 120° C. for 24 hours to prepare the microsphere molecular sieve catalyst S-3.

The particle size of the catalyst was concentrated within a range of 55-120 μm.

Preparation Example 4

(1) 725 kg of ethanol with a content of 95 wt % and 305 kg of tetrapropylammonium hydroxide aqueous solution with a content of 22.5 wt % were respectively added into a 2 m$^3$ stainless steel reaction kettle, and subjected to stirring, 347 kg of ethyl orthosilicate was added, the mixture was further stirred, 330 kg of water and 12.1 g of Ce(NO$_3$)$_3$.7H$_2$O were subsequently added, the mixture was subjected to continuous agitation at room temperature for 4 hours to form a colloid mixture, wherein the molar ratio of ethyl orthosilicate calculated by SiO$_2$:ethanol:tetrapropylammonium hydroxide:water was 1:13:0.2:20; the weight ratio of ethyl orthosilicate calculated by SiO$_2$ relative to metal source calculated by metal elements was 26700:1.

(2) The colloid mixture was fed into a reaction kettle, and subjected to crystallizing in an ethanol-hydrothermal system, wherein the crystallization conditions comprise: subjected to crystallizing at 65° C. for 1 day, and crystallizing at 120° C. for 2 days, so as to obtain a crystallization mother liquor with the pH of 13.55;

(3) The obtained crystallization mother liquor was subjected to an ethanol removal treatment at the temperature of 85° C. for 10 hours, water was continuously supplemented during the treatment process, the materials were maintained at a certain liquid level, an aqueous ethanol gas phase material flow was recovered for later use, the recovering process of ethanol was same as the Preparation Example 1; the product obtained by ethanol removing treatment was then subjected to washing and concentrating with a 50 nm six-tube membrane, and subjected to washing with water at the temperature of 40-60° C. with the used amount of 6.5 m³, until the pH value of the washing water for the crystallization product reached 9.0. 452 kg of molecular sieve slurry with the solid content of 23.4 wt % was obtained after the washing and concentration process;

A small amount of the molecular sieve slurry was taken and subjected to drying at 120° C. for 20 hours, the molecular sieve slurry was then subjected to roasting at 550° C. for 6 hours to produce the molecular sieve, wherein the molecular sieve had a content of metal elements of 36.6 μg/g, the BET specific surface area of 431 m²/g, and the external specific surface area of 49 m²/g;

The X-ray diffraction (XRD) spectrum of the molecular sieve had the characteristics consistent with those of the MFI structure standard XRD spectrum illustrated on the literature *Micropore Materials*, Vol. 22, p 63'7, 1998, it demonstrated that the molecular sieve had the MFI crystal structure;

The TEM photo showed that the molecular sieve with a MFI topological structure exhibited uniform crystal grain particle size, the particle size was within a range of 0.1-0.2 μm;

(4) The part of the molecular sieve slurry obtained in step (3) was mixed with 129 kg of alkaline silica sol with the content of 30 wt % (the pH value was 9.5, the content of sodium ions was 324 ppm, the content of $SiO_2$ was 40 wt %, and the surface area of $SiO_2$ obtained after roasting was 225 m²/g), wherein the weight ratio of the molecular sieve based on the dry weight in the molecular sieve slurry relative to the alkaline silica sol calculated by $SiO_2$ was 70:30; 10 kg of water was further added, the mixture was stirred uniformly and pulped to obtain molecular sieve-binder mixed slurry with the solid content of 24.5 wt %. The molecular sieve-binder mixed slurry was conveyed to a mist spray forming device for performing the mist spray forming, wherein the inlet temperature and the outlet temperature were 260° C. and 125° C. respectively. The mixture was then fed into a 3 m³ heating shuttle furnace, was subjected to roasting at 280° C., 400° C. and 480° C. for 2 h respectively, and was finally subjected to roasting at 550° C. for 12 h to obtain 142.7 kg microsphere molecular sieve, wherein the content of the silicon molecular sieve having a MFI topological structure and containing metal ions with extremely trace Lewis acid characteristic was 70 wt %, and the content of the binder calculated by $SiO_2$ was 30 wt %;

100 kg of the microsphere molecular sieve and 1,000 kg of an alkaline buffer solution of a nitrogen-containing compound (the alkaline buffer solution of a nitrogen-containing compound was a mixed solution of ammonia water and an ammonium nitrate aqueous solution, wherein the pH value was 11.35, the content of the ammonia water was 26 wt %, the content of the ammonium nitrate in the ammonium nitrate aqueous solution was 7.5 wt %, the weight ratio of the ammonia water relative to the ammonium nitrate aqueous solution was 3:2) were added into a 2 m³ stainless steel reaction kettle, the mixture was subjected to stirring at a constant temperature of 85° C. and under the pressure of 2.6 kg/cm² for 2 hours, then subjected to filtering, and drying at 90° C. for 12 hours, the treatments were repeated once under the same conditions, subjected to filtering, and washing until the pH of a filtration clear solution was about 9, and subsequently subjected to drying at 120° C. for 24 hours to prepare the microsphere molecular sieve catalyst S-4.

The particle size of the catalyst was concentrated within a range of 70-150 μm.

Preparation Example 5

The molecular sieve was prepared according to the same method of the Preparation Example 1, except that the metal source was replaced with tetrabutyl titanate, and the weight ratio of ethyl orthosilicate calculated by $SiO_2$ relative to metal source calculated by metal elements was 50000:1.

The content of metal elements in the prepared molecular sieve was 19.2 μg/g. The product was labeled as the microsphere molecular sieve catalyst S-5.

The following examples illustrate the preparation method of caprolactam according to the present disclosure.

Example 1

Preparation of caprolactam crude product: the gas phase Beckmann rearrangement reaction of cyclohexanone oxime was performed in a fluidized bed reactor and a fixed bed reactor which were connected in series, the vertical stainless steel fluidized bed reactor with a volume of 316 L has a diameter of the upper section of 20 cm, a diameter of the lower section of 10 cm, the lengths of the upper section and the lower section of the fluidized bed reactor were 60 cm and 80 cm respectively; the loading amount of the microsphere molecular sieve catalyst S-1 prepared in the Preparation Example 1 in the fluidized bed reactor was 300 g. The fluidized bed reactor was also in communication with a vertical stainless steel regeneration reactor with a volume of 316 L, which was used for regenerating and recycling the catalyst flowing out of the fluidized bed reactor, the regeneration reactor had a diameter of 15 cm and a length of 160 cm, and the loading amount of the catalyst was 550 g. The reaction conditions in the fluidized bed reactor comprise: the reaction pressure was 0.1 MPa, the reaction temperature of the fluidized bed was 380° C., the gas was fed in an atomizing and spraying manner, the temperature of a vaporization chamber was controlled at 190° C., the lowest temperature point of the vaporizer was 160° C., the temperature of an outlet pipeline was preserved at 250° C., the weight hourly space velocity (WHSV) of the cyclohexanone oxime was 5 h$^{-1}$, the flow rate of nitrogen gas was 0.8 m³/h, the cyclohexanone oxime accounts for 35 wt % of the total amount of the cyclohexanone oxime and the ethanol, and the water accounted for 0.4 wt % of the total amount of water, ethanol and cyclohexanone oxime. The fluidized bed reactor was connected with and followed by a fixed bed reactor, and the loading amount of the spherical molecular sieve catalyst S-2 prepared in the Preparation Example 2 in the fixed bed reactor was 80 g. The reaction temperature of the fixed bed reactor was 380° C. and the pressure was 0.5 atm (absolute pressure).

The product obtained after the gas phase Beckmann rearrangement reaction was subjected to heat exchange (firstly carrying out water cooling, and then carrying out cooling by circulating with an ethylene glycol solution at the temperature of −10° C.), a reaction product was collected to obtain an ethanol solution mixture containing caprolactam, wherein the gas phase rearrangement reaction was performed for 72 hours, the reaction conversion rate of cyclohexanone oxime was more than 99.88%, the total selectivity of caprolactam was higher than 95.6%, the content of ethyl-epsilon-caprolactam condensation compound was about 1.0 wt % (the compound was converted into caprolactam through hydrolysis reaction), the content of light components (substances with the boiling point lower than that of caprolactam) in the ethanol solution mixture containing caprolactam was about 3.0 wt %, and the content of heavy components (substances with the boiling point higher than that of caprolactam) was about 0.5 wt %. Other major and important by-products include: cyclohexene compounds, nitrile compounds, ketone compounds, amide compounds, aniline compounds, 2-ethylpyridine, 5-hexenoic acid ethyl ester, 4-hexenoic acid ethyl ester, 5-cyano-1-pentene, cyanocyclopentane, cyclohexenone, cyclohexanol, nitrobenzene, furan, phenol, N-ethyl-caprolactam and other light components, and octahydroacridine, octahydrophenazine, tetrahydronaphthylamine, phenazine, tetrahydrocarbazole and other heavy components. The results of the reaction at different reaction times were shown in Table 1.

800 g of the mixture was taken, the solvent (ethanol) was recovered by using a rotary evaporator, so as to obtain 514 g of an aqueous ethanol gas phase material flow (which was recycled after dehydration) and 283.3 g of crude caprolactam containing heavy impurities having a boiling point higher than that of caprolactam and light impurities having a boiling point lower than that of caprolactam.

Removing light impurities: the crude caprolactam was subjected to vacuum distillation under the pressure (absolute pressure) of 1.7 kPa, the crude caprolactam was heated from room temperature (20° C.) to 100° C. at a temperature rise speed of 2° C./min and the temperature was maintained at 100° C. for 30 min, the tower top did not have a reflux, the temperature was further increased to 150° C. at a temperature rise speed of 2° C./min, the pressure was directly reduced to 0.47 kPa, reflux ratio at the tower top was 1:30, until there was not distilled light components, so as to obtain 269.8 g of light component removal product (kettle bottom materials). Chromatographic analysis result showed that the light component removal product comprise the main ingredients as follows: 98.3 wt % of caprolactam, 484 µg/g of 5-cyano-1-pentene, 150 µg/g of cyclohexanone oxime, 1,145 µg/g of cyclohexenone, 390 µg/g of N-ethyl-caprolactam, 435 µg/g of octahydrophenazine, 390 µg/g of tetrahydroazepin-2-ketone and its isomers, 1,040 µg/g of decahydrophenazine, 80 µg/g of 5,6,7,8-tetrahydronaphthylamine, 60 µg/g of tetrahydrocarbazole and other undefined impurities. The obtained reaction product of epsilon-caprolactam was analyzed on a gas chromatograph with a model number 7890B manufactured by the Agilent Technologies Inc. In order to obtain enough refined raw materials for crystallization, the operations of rotary evaporation of the gas phase rearrangement reaction products and removing light impurities were repeated once, about 540 g of light component removal product was obtained.

Crystallization (Crystallization Solvent Containing Ethanol)

The obtained crude caprolactam (300 parts by weight), and a mixed solvent consisting of ethanol (10 parts by weight), n-heptane (297 parts by weight) and isopropyl ether (593 parts by weight) (alkane:ether=1:2 parts by weight) (the crystallization solvent was in total of 900 parts by weight) were fully mixed in an adiabatic crystallization kettle at 62° C. until the crude caprolactam was completely dissolved in the solvent, the temperature in the crystallization kettle was then slowly lowered to 60° C., the interior of the crystallization kettle was vacuumized for performing evaporative crystallization under an operating pressure of 60 kPa, the evaporation amount was controlled in order to uniformly evaporate the solvent; the temperature of a liquid phase in the crystallization kettle was reduced along with the continuous volatilization of the solvent, when the temperature of the solution in the crystallizer was reduced to 55° C., the operation pressure was modified to 45 kPa, the precipitation of crystals was started at 53° C., the vacuumizing process was continued to carry out evaporative crystallization; when the temperature of the solution in the crystallizer was reduced to 50° C., the operation pressure was modified to 33 kPa; when the temperature of the solution in the crystallization kettle was further lowered to 45° C., the operation pressure was modified to 28 kPa until the temperature of the solution in the crystallizer was reduced to 40° C., the solution was continuously kept for aging for 45 min, and the experiment was stopped. The obtained caprolactam slurry (1,200 parts by weight) was sent from the crystallizer to a centrifuge for performing solid-liquid separation, the resulting solid phase was washed with a mixed solvent (245 parts by weight; about 40° C.) having the same components in the same proportions as defined above to obtain caprolactam crystals (241 parts by weight) and a liquid phase (about 1,200 parts by weight).

The obtained caprolactam crystals (240 parts by weight), and the mixed solvent consisting of ethanol (8 parts by weight), n-heptane (237 parts by weight) and isopropyl ether (475 parts by weight) (alkane:ether=1:2 by weight) were poured into a crystallizer with a jacket and the temperature kept at 62° C., the above operation was repeated until the temperature of the solution in the crystallizer was reduced to 40° C., the solution was continuously kept for aging for 45 min, the obtained caprolactam slurry (about 960 parts by weight) was conveyed from the crystallizer to a centrifuge for performing solid-liquid separation, the resulting solid phase was washed with a mixed solvent (200 parts by weight; about 40° C.) having the same components in the same proportions as defined above to obtain caprolactam crystals (about 197.6 parts by weight, with a purity of 99.9947 wt %) and a liquid phase (about 960 parts by weight).

Hydrogenation, Evaporation and Distillation

Hydrogenation reaction: 150 g of caprolactam crystals (with a purity of 99.9947 wt %) was added into a 500 mL reaction kettle, 37.5 g of water was added, 1.5 g of Raney Ni catalyst as a hydrogenation catalyst (Raney nickel catalyst, commercially available from Jiangsu Feima Catalyst Co., Ltd., under the brand name FMR series) was further added, the mixture was heated to about 75° C., hydrogen gas was introduced, the hydrogen gas flow rate was controlled at 100 mL/min, the reaction pressure was maintained at 0.7 MPa, such that the aqueous solution of the caprolactam crystals was contacted with the hydrogen gas to carry out reaction for 1 hour. The mixture was then evaporated on a rotary evaporator to dehydrate (−0.09 MPa, 80° C.), and subjected to vacuum distillation at about 1 mmHg to yield 130 g of caprolactam product, the distillation was then stopped. The quality of the obtained caprolactam product was analyzed, the analysis results showed that the purity of the caprolactam was 99.9976 wt %, the PM value was 39600 s, the VB was 0.030 mmol/kg, the E value was 0.025, the chromatic value was 0, and the alkalinity was 0.02 mmol/kg.

Comparative Example 1

The preparation of crude caprolactam product was carried out according to the same method of Example 1, except that the methanol was used for replacing the ethanol as the reaction solvent, and that water accounted for 1.2 wt % of the total amount of water, methanol and cyclohexanone oxime. The results of the reaction at different reaction times were shown in Table 2.

800 g of mixture was taken, the solvent (methanol) was recovered by using a rotary evaporator so as to obtain 309.3 g of caprolactam crude product containing heavy impurities with boiling points higher than caprolactam and light impurities with boiling points lower than caprolactam; the caprolactam crude product was subjected to analyzing, analysis result showed that the caprolactam crude product comprise the main ingredients as follows: 95.8 wt % of caprolactam, 4,840 µg/g of 5-cyano-1-pentene, 150 µg/g of cyclohexanone oxime, 4,845 µg/g of cyclohexenone, 435 µg/g of octahydrophenazine, 390 µg/g of tetrahydroazepin-2-ketone and its isomers, 1,040 µg/g of decahydrophenazine and other undefined impurities.

Removing light impurities: the crude caprolactam was subjected to vacuum distillation under the pressure (absolute pressure) of 1.7 kPa, the crude caprolactam was heated from room temperature (20° C.) to 100° C. at a temperature rise speed of 2° C./min and the temperature was maintained at 100° C. for 30 min, the tower top did not have a reflux, the temperature was further increased to 150° C. at a temperature rise speed of 2° C./min, the pressure was directly reduced to 0.47 kPa, reflux ratio at the tower top was 1:30, until there was not distilled light components, so as to obtain 275 g of light component removal product (kettle bottom materials). Chromatographic analysis result showed that the light component removal product comprise the main ingredients as follows: 98.4 wt % of caprolactam, 270 µg/g of 5-cyano-1-pentene, 260 µg/g of cyclohexanone oxime, 1,500 µg/g of cyclohexenone, 1,100 µg/g of N-ethyl-caprolactam, 470 µg/g of octahydrophenazine, 560 µg/g of tetrahydroazepin-2-ketone and its isomers, 1,200 µg/g of decahydrophenazine and other undefined impurities. In order to obtain enough refined raw materials for crystallization, the operations of rotary evaporation of the gas phase rearrangement reaction products and removing light impurities were repeated once, about 550 g of light component removal product was obtained.

Crystallization (Crystallization Solvent Containing Ethanol)

The obtained crude caprolactam (300 parts by weight), and a mixed solvent consisting of ethanol (10 parts by weight), n-heptane (297 parts by weight) and isopropyl ether (593 parts by weight) (alkane:ether=1:2 parts by weight) (the crystallization solvent was in total of 900 parts by weight) were fully mixed in an adiabatic crystallization kettle at 62° C. until the crude caprolactam was completely dissolved in the solvent, the temperature in the crystallization kettle was then slowly lowered to 60° C., the interior of the crystallization kettle was vacuumized for performing evaporative crystallization under an operating pressure of 60 kPa, (the evaporation amount was controlled in order to uniformly evaporate the solvent); the temperature of a liquid phase in the crystallization kettle was reduced along with the continuous volatilization of the solvent, when the temperature of the solution in the crystallizer was reduced to 55° C., the operation pressure was modified to 45 kPa, the precipitation of crystals was started at 53° C., the vacuumizing process was continued to carry out evaporative crystallization; when the temperature of the solution in the crystallizer was reduced to 50° C., the operation pressure was modified to 33 kPa; when the temperature of the solution in the crystallization kettle was further lowered to 45° C., the operation pressure was modified to 28 kPa until the temperature of the solution in the crystallizer was reduced to 40° C., the solution was continuously kept for aging for 45 min, and the experiment was stopped. The obtained caprolactam slurry (1,200 parts by weight) was sent from the crystallizer to a centrifuge for performing solid-liquid separation, the resulting solid phase was washed with a mixed solvent (245 parts by weight; about 40° C.) having the same components in the same proportions as defined above to obtain caprolactam crystals (240 parts by weight) and a liquid phase (about 1,200 parts by weight).

The obtained caprolactam crystals (240 parts by weight), and a mixed solvent consisting of ethanol (8 parts by weight), n-heptane (237 parts by weight) and isopropyl ether (475 parts by weight) (alkane:ether=1:2 by weight) were poured into a crystallizer with a jacket and the temperature kept at 62° C., the above operation was repeated until the temperature of the solution in the crystallizer was reduced to 40° C., the solution was continuously kept for aging for 45 min, the obtained caprolactam slurry (about 960 parts by weight) was conveyed from the crystallizer to a centrifuge for performing solid-liquid separation, the resulting solid phase was washed with a mixed solvent (200 parts by weight; about 40° C.) having the same components in the same proportions as defined above to obtain caprolactam crystals (about 197 parts by weight, with a purity of 99.9944%) and a liquid phase (about 960 parts by weight).

Hydrogenation, Evaporation and Distillation 150 g of caprolactam crystals (with a purity of 99.9944 wt %) were subjected to hydrogenation, evaporation and distillation according to the method of Example 1. Distillation was stopped after 130 g of caprolactam product had been obtained. The quality of the obtained caprolactam product was analyzed, the analysis results showed that the purity of the caprolactam was 99.9966 wt %, the PM value was 36000 s, the VB was 0.035 mmol/kg, the E value was 0.034, the chromatic value was 0, and the alkalinity was 0.03 mmol/kg.

Comparative Example 2

The preparation of crude caprolactam product was carried out according to the same method of Example 1, except that the crystallization process included: The obtained crude caprolactam (300 parts by weight), and a mixed solvent consisting of n-heptane (300 parts by weight) and isopropyl ether (600 parts by weight) (alkane:ether=1:2 parts by weight) (the crystallization solvent was in total of 900 parts by weight) were fully mixed in an adiabatic crystallization kettle at 62° C. until the crude caprolactam was completely dissolved in the solvent, the temperature in the crystallization kettle was then slowly lowered to 60° C., the interior of the crystallization kettle was vacuumized for performing evaporative crystallization under an operating pressure of 60 kPa, (the evaporation amount was controlled in order to uniformly evaporate the solvent); the temperature of a liquid phase in the crystallization kettle was reduced along with the continuous volatilization of the solvent, when the temperature of the solution in the crystallizer was reduced to 55° C., the operation pressure was modified to 45 kPa, the precipitation of crystals was started at 51.5° C. (lower than the temperature of crystal precipitation of Example 1), the vacuumizing process was continued to carry out evaporative crystallization; when the temperature of the solution in the crystallizer was reduced to 50° C., the operation pressure was modified to 33 kPa; when the temperature of the solution in the crystallization kettle was further lowered to 45° C., the operation pressure was modified to 28 kPa until the temperature of the solution in the crystallizer was reduced to 40° C., the solution was continuously kept for aging for 45 min, and the experiment was stopped. The obtained caprolactam slurry (1,200 parts by weight) was sent from the crystallizer to a centrifuge for performing solid-liquid separation, the resulting solid phase was washed with a mixed solvent (254 parts by weight; about 40° C.) having the same components in the same proportions as defined above to obtain caprolactam crystals (249 parts by weight) and a liquid phase (about 1,200 parts by weight).

The obtained caprolactam crystals (240 parts by weight), and a mixed solvent consisting of n-heptane (240 parts by weight) and isopropyl ether (480 parts by weight) (alkane:ether=1:2 by weight) were poured into a crystallizer with a jacket and the temperature kept at 62° C., the above operation was repeated until the temperature of the solution in the crystallizer was reduced to 40° C., the solution was continuously kept for aging for 45 min, the obtained caprolactam slurry (about 998 parts by weight) was conveyed from the crystallizer to a centrifuge for performing solid-liquid separation, the resulting solid phase was washed with a mixed solvent (206 parts by weight; about 40° C.) having the same components in the same proportions as defined above to obtain caprolactam crystals (about 203.4 parts by weight, with a purity of 99.9933 wt %) and a liquid phase (about 960 parts by weight). There is obviously the phenomenon of scabbing on the inner wall and the stirring blade of the crystallization kettle.

The hydrogenation, evaporation and distillation were performed according to the same manner as Example 1. The quality of the obtained caprolactam product was analyzed, the analysis results showed that the purity of the caprolactam was 99.9946 wt %, the PM value was 31600 s, the VB was 0.036 mmol/kg, the E value was 0.033, the chromatic value was 3, and the alkalinity was 0.04 mmol/kg.

Comparative Example 3

The preparation of crude caprolactam product was carried out according to the same method of Example 1, except that during the crystallization, the crystallization solvent was isopropyl ether. The crystallization process specifically comprises:

The obtained crude caprolactam (300 parts by weight) and solvent isopropyl ether (900 parts by weight) were fully mixed in an adiabatic crystallization kettle at 62° C. until the crude caprolactam was completely dissolved in the solvent, the temperature in the crystallization kettle was then slowly lowered to 60° C., the interior of the crystallization kettle was vacuumized for performing evaporative crystallization under an operating pressure of 60 kPa, (the evaporation amount was controlled in order to uniformly evaporate the solvent); the temperature of a liquid phase in the crystallization kettle was reduced along with the continuous volatilization of the solvent, when the temperature of the solution in the crystallizer was reduced to 55° C., the operation pressure was modified to 45 kPa, the precipitation of crystals was started at 53° C., the vacuumizing process was continued to carry out evaporative crystallization; when the temperature of the solution in the crystallizer was reduced to 50° C., the operation pressure was modified to 33 kPa; when the temperature of the solution in the crystallization kettle was further lowered to 45° C., the operation pressure was altered to 28 kPa until the temperature of the solution in the crystallizer was reduced to 40° C., the solution was continuously kept for aging for 45 min, and the experiment was stopped. The obtained caprolactam slurry (1,200 parts by weight) was sent from the crystallizer to a centrifuge for performing solid-liquid separation, the resulting solid phase was washed with isopropyl ether (240 parts by weight; about 40° C.) to obtain caprolactam crystals (230 parts by weight) and a liquid phase (about 1,200 parts by weight).

The obtained caprolactam crystals (220 parts by weight), and the solvent isopropyl ether (660 parts by weight) were poured into a crystallizer with a jacket and the temperature kept at 62° C., the above operation was repeated until the temperature of the solution in the crystallizer was reduced to 40° C., the solution was continuously kept for aging for 45 min, the obtained caprolactam slurry (about 880 parts by weight) was conveyed from the crystallizer to a centrifuge for performing solid-liquid separation, the resulting solid phase was washed with isopropyl ether (170 parts by weight; about 40° C.) to obtain caprolactam crystals (about 168.7 parts by weight, with a purity of 99.9955 wt %) and a liquid phase (about 880 parts by weight).

The quality of the obtained caprolactam product was analyzed, the analysis results showed that the purity of the caprolactam was 99.9955 wt %, the PM value was 36000 s, the VB was 0.032 mmol/kg, the E value was 0.024, the chromatic value was 3, and the alkalinity was 0.03 mmol/kg.

Example 2

The preparation of crude caprolactam product was carried out according to the same method of Example 1, except that the catalyst of Preparation Example 1 was replaced with the catalyst of Preparation Example 3. The gas phase rearrangement reaction was performed in the same manner as that in the part of the Example 1, the gas phase rearrangement reaction was carried out for 60 hours, the reaction conversion rate of the cyclohexanone oxime was more than 99.83%, the total selectivity of the caprolactam was more than 95.2%, and the heavy components were slightly increased. The process for removing light impurities, hydrogenation, evaporation and distillation was performed in the same manner as Example 1. The crystallization process specifically comprises:

The obtained crude caprolactam (300 parts by weight), and a mixed solvent consisting of ethanol (20 parts by weight), n-heptane (290 parts by weight) and isopropyl ether (590 parts by weight) (alkane:ether=1:2 parts by weight) (the crystallization solvent was in total of 900 parts by weight) were fully mixed in an adiabatic crystallization kettle at 62° C. until the crude caprolactam was completely dissolved in the solvent, the temperature in the crystallization kettle was then slowly lowered to 60° C., the interior of the crystallization kettle was vacuumized for performing evaporative crystallization under an operating pressure of 60 kPa, (the evaporation amount was controlled in order to uniformly evaporate the solvent); the temperature of a liquid phase in the crystallization kettle was reduced along with the continuous volatilization of the solvent, when the temperature of the solution in the crystallizer was reduced to 55° C., the operation pressure was modified to 45 kPa, the precipitation of crystals was started at 54° C., the vacuumizing process was continued to carry out evaporative crystallization; when the temperature of the solution in the crystallizer was reduced to 50° C., the operation pressure was modified to 33 kPa; when the temperature of the solution in the crystallization kettle was further lowered to 45° C., the operation pressure was modified to 28 kPa until the temperature of the solution in the crystallizer was reduced to 40° C., the operation pressure was altered to 23 kPa until the temperature of the solution in the crystallizer was reduced to 30° C., the solution was continuously kept for aging for 45 min, and the experiment was stopped. The obtained caprolactam slurry (1,200 parts by weight) was sent from the crystallizer to a centrifuge for performing solid-liquid separation, the resulting solid phase was washed with a mixed solvent (230 parts by weight; about 30° C.) having the same components in the same proportions as defined above to obtain caprolactam crystals (221.5 parts by weight) and a liquid phase (about 1,200 parts by weight).

The obtained caprolactam crystals (220 parts by weight), and a mixed solvent consisting of ethanol (13.2 parts by weight), n-heptane (214 parts by weight) and isopropyl ether (432 parts by weight) (alkane:ether=1:2 by weight) were poured into a crystallizer with a jacket and the temperature kept at 62° C., the above operation was repeated until the temperature of the solution in the crystallizer was reduced to 30° C., the solution was continuously kept for aging for 45 min, the obtained caprolactam slurry (about 880 parts by weight) was conveyed from the crystallizer to a centrifuge for performing solid-liquid separation, the resulting solid phase was washed with a mixed solvent (170 parts by weight; about 30° C.) having the same components in the same proportions as defined above to obtain caprolactam crystals (about 167.7 parts by weight, with a purity of 99.9961 wt %) and a liquid phase (about 880 parts by weight).

The quality of the obtained caprolactam product was analyzed, the analysis results showed that the purity of the caprolactam was 99.9978 wt %, the PM value was 43200 s, the VB was 0.022 mmol/kg, the E value was 0.017, the chromatic value was 0, and the alkalinity was 0.013 mmol/kg.

Example 3

The preparation of crude caprolactam product was carried out according to the same method of Example 1, except that the catalyst of Preparation Example 1 was replaced with the catalyst of Preparation Example 4. The gas phase rearrangement reaction was performed in the same manner as that in the part of the Example 1, the gas phase rearrangement reaction was carried out for 72 hours, the reaction conversion rate of the cyclohexanone oxime was more than 99.86%, and the total selectivity of the caprolactam was more than 95.6%. The process for removing light impurities, hydrogenation, evaporation and distillation was performed in the same manner as Example 1. The crystallization process specifically comprises:

The obtained crude caprolactam (300 parts by weight), and a mixed solvent consisting of ethanol (10 parts by weight) and isopropyl ether (890 parts by weight) (the crystallization solvent was in total of 900 parts by weight) were fully mixed in an adiabatic crystallization kettle at 62° C. until the crude caprolactam was completely dissolved in the solvent, the temperature in the crystallization kettle was then slowly lowered to 60° C., the interior of the crystallization kettle was vacuumized for performing evaporative crystallization under an operating pressure of 65 kPa, (the evaporation amount was controlled in order to uniformly evaporate the solvent); the temperature of a liquid phase in the crystallization kettle was reduced along with the continuous volatilization of the solvent, when the temperature of the solution in the crystallizer was reduced to 50° C., the operation pressure was modified to 53 kPa, the vacuumizing process was continued to carry out evaporative crystallization; when the temperature of the solution in the crystallizer was reduced to 45° C., the operation pressure was modified to 50 kPa; the precipitation of crystals was started at 43° C., when the temperature of the solution in the crystallization kettle was further lowered to 40° C., the operation pressure was modified to 40 kPa until the temperature of the solution in the crystallizer was reduced to 35° C., the solution was continuously kept for aging for 45 min, and the experiment was stopped. The obtained caprolactam slurry (1,200 parts by weight) was sent from the crystallizer to a centrifuge for performing solid-liquid separation, the resulting solid phase was washed with a mixed solvent (250 parts by weight; about 35° C.) having the same components in the same proportions as defined above to obtain caprolactam crystals (245 parts by weight) and a liquid phase (about 1,200 parts by weight).

The obtained caprolactam crystals (240 parts by weight), and a mixed solvent consisting of ethanol (8 parts by weight) and isopropyl ether (712 parts by weight) were poured into a crystallizer with a jacket and the temperature kept at 62° C., the above operation was repeated until the temperature of the solution in the crystallizer was reduced to 35° C., the solution was continuously kept for aging for 45 min, the obtained caprolactam slurry (about 960 parts by weight) was conveyed from the crystallizer to a centrifuge for performing solid-liquid separation, the resulting solid phase was washed with a mixed solvent (200 parts by weight; about 35° C.) having the same components in the same proportions as defined above to obtain caprolactam crystals (about 199.6 parts by weight, with a purity of 99.9947 wt %) and a liquid phase (about 960 parts by weight).

The quality of the obtained caprolactam product was analyzed, the analysis results showed that the purity of the caprolactam was 99.9961 wt %, the PM value was 39600 s, the VB was 0.032 mmol/kg, the E value was 0.026, the chromatic value was 0, and the alkalinity was 0.02 mmol/kg.

Example 4

The preparation of crude caprolactam product was carried out according to the same method of Example 1, except that the catalyst of Preparation Example 1 was replaced with the catalyst of Preparation Example 5. The gas phase rearrangement reaction was performed for 72 hours, the reaction conversion rate of the cyclohexanone oxime was more than 99.86%, the total selectivity of the caprolactam was more than 95.6%. The process for removing light impurities, hydrogenation, evaporation and distillation was performed in the same manner as Example 1. The crystallization process specifically comprises:

The obtained crude caprolactam (300 parts by weight), and a mixed solvent consisting of ethanol (10 parts by weight) and n-heptane ether (890 parts by weight) (the crystallization solvent was in total of 900 parts by weight) were fully mixed in an adiabatic crystallization kettle at 62° C. until the crude caprolactam was completely dissolved in the solvent, the temperature in the crystallization kettle was then slowly lowered to 60° C., the interior of the crystallization kettle was vacuumized for performing evaporative crystallization under an operating pressure of 26 kPa, (the evaporation amount was controlled in order to uniformly evaporate the solvent); the temperature of a liquid phase in the crystallization kettle was reduced along with the continuous volatilization of the solvent, when the temperature of the solution in the crystallizer was reduced to 57° C., an oil precipitation phenomenon appeared, when the temperature was continuously reduced to 56° C., precipitation of crystals was started; the solution slowly became limpid, when the temperature of the solution in the crystallizer was reduced to 50° C., the operation pressure was changed to 20 kPa, the vacuumizing process was continued to carry out evaporative crystallization; when the temperature of the solution in the crystallizer was reduced to 45° C., the operation pressure was modified to 17 kPa; when the temperature of the solution in the crystallization kettle was further lowered to 40° C., the operation pressure was altered to 13 kPa until the temperature of the solution in the crystallizer was reduced to 35° C., the solution was continuously kept for aging for 45 min, and the experiment was stopped. The obtained caprolactam slurry (1,200 parts by weight) was sent from the crystallizer to a centrifuge for performing solid-liquid separation, the resulting solid phase was washed with a mixed solvent (260 parts by weight; about 35° C.) having the same components in the same proportions as defined above to obtain caprolactam crystals (266 parts by weight) and a liquid phase (about 1,200 parts by weight).

The obtained caprolactam crystals (250 parts by weight), and a mixed solvent consisting of ethanol (8 parts by weight) and n-heptane (742 parts by weight) were poured into a crystallizer with a jacket and the temperature kept at 62° C., the above operation was repeated, an oil precipitation phenomenon still emerged in the process until the temperature of the solution in the crystallizer was reduced to 35° C., the solution was kept for aging for 45 min, the obtained caprolactam slurry (about 960 parts by weight) was conveyed from the crystallizer to a centrifuge for performing solid-liquid separation, the resulting solid phase was washed with a mixed solvent (230 parts by weight; about 35° C.) having the same components in the same proportions as defined above to obtain caprolactam crystals (about 225.6 parts by weight, with a purity of 99.9847 wt %) and a liquid phase (about 1,000 parts by weight).

The quality of the obtained caprolactam product was analyzed, the analysis results showed that the purity of the caprolactam was 99.9894 wt %, the PM value was 1800 s, the VB was 0.48 mmol/kg, the E value was 0.075, the chromatic value was 5, and the alkalinity was 0.33 mmol/kg.

Example 5

The preparation of crude caprolactam product was carried out according to the same method of Example 1, except that in the crystallization process, the content of ethanol in the crystallization solvent was 5 wt %, and the weight ratio of n-heptane:isopropyl ether was 1:2, the final crystallization temperature was 30° C. The crystallization process specifically comprises:

The obtained crude caprolactam (300 parts by weight), and a mixed solvent consisting of ethanol (45 parts by weight), n-heptane (285 parts by weight) and isopropyl ether (570 parts by weight) (alkane:ether=1:2 parts by weight) (the crystallization solvent was in total of 900 parts by weight) were fully mixed in an adiabatic crystallization kettle at 60° C. until the crude caprolactam was completely dissolved in the solvent, the temperature in the crystallization kettle was then slowly lowered to 58° C., the interior of the crystallization kettle was vacuumized for performing evaporative crystallization under an operating pressure of 62 kPa, the evaporation amount was controlled in order to uniformly evaporate the solvent; the temperature of a liquid phase in the crystallization kettle was reduced along with the continuous volatilization of the solvent; when the temperature of the solution in the crystallizer was reduced to 55° C., the operation pressure was modified to 55 kPa, the vacuumizing process was continued to carry out evaporative crystallization; when the temperature of the solution in the crystallizer was reduced to 50° C., the operation pressure was changed to 48 kPa; when the temperature of the solution in the crystallizer was further reduced to 45° C., the operation pressure was altered to 40 kPa; when the temperature was lowered to 41° C., the precipitation of crystals was started; when the temperature of the solution in the crystallization kettle was further lowered to 40° C., the operation pressure was modified to 36 kPa; the temperature of the solution in the crystallizer was reduced to 30° C., the solution was continuously kept for aging for 45 min, and the experiment was stopped. The obtained caprolactam slurry (1,200 parts by weight) was sent from the crystallizer to a centrifuge for performing solid-liquid separation, the resulting solid phase was washed with a mixed solvent (170 parts by weight; about 30° C.) having the same components in the same proportions as defined above to obtain caprolactam crystals (about 168 parts by weight, with a purity of 99.9975 wt %) and a liquid phase (about 1,200 parts by weight).

The quality of the obtained caprolactam product was analyzed, the analysis results showed that the purity of the caprolactam was 99.9984 wt %, the PM value was 45000 s, the VB was 0.021 mmol/kg, the E value was 0.018, the chromatic value was 0, and the alkalinity was 0.02 mmol/kg. The caprolactam product quality was improved, but the caprolactam yield was obviously reduced.

Example 6

The preparation of crude caprolactam product was carried out according to the same method of Example 1, except that the alkane solvent was not used in the crystallization solvent, the crystallization process specifically comprises:

The obtained crude caprolactam (300 parts by weight), and a mixed solvent consisting of ethanol (5 parts by weight) and isopropyl ether (895 parts by weight) (the crystallization solvent was in total of 900 parts by weight) were fully mixed in an adiabatic crystallization kettle at 62° C. until the crude caprolactam was completely dissolved in the solvent, the temperature in the crystallization kettle was then slowly lowered to 60° C., the interior of the crystallization kettle was vacuumized for performing evaporative crystallization under an operating pressure of 65 kPa, (the evaporation amount was controlled in order to uniformly evaporate the solvent); the temperature of a liquid phase in the crystallization kettle was reduced along with the continuous volatilization of the solvent, when the temperature of the solution in the crystallizer was reduced to 50° C., the operation pressure was modified to 53 kPa, the vacuumizing process was continued to carry out evaporative crystallization; when the temperature of the solution in the crystallizer was reduced to 45° C., the operation pressure was modified to 50 kPa; the precipitation of crystals was started at 43° C. and the crystallization process was continued; when the temperature of the solution in the crystallization kettle was further lowered to 40° C., the operation pressure was modified to 40 kPa until the temperature of the solution in the crystallizer was reduced to 35° C., the solution was continuously kept for aging for 45 min, and the experiment was stopped. The obtained caprolactam slurry (1,200 parts by weight) was sent from the crystallizer to a centrifuge for performing solid-liquid separation, the resulting solid phase was washed with a mixed solvent (250 parts by weight; about 35° C.) having the same components in the same proportions as defined above to obtain caprolactam crystals (248 parts by weight) and a liquid phase (about 1,200 parts by weight).

The obtained caprolactam crystals (240 parts by weight), and a mixed solvent consisting of ethanol (4 parts by weight) and isopropyl ether (712 parts by weight) were poured into a crystallizer with a jacket and the temperature kept at 62° C., the above operation was repeated until the temperature of the solution in the crystallizer was reduced to 35° C., the solution was continuously kept for aging for 45 min, the obtained caprolactam slurry (about 960 parts by weight) was conveyed from the crystallizer to a centrifuge for performing solid-liquid separation, the resulting solid phase was washed with a mixed solvent (200 parts by weight; about 35° C.) having the same components in the same proportions as defined above to obtain caprolactam crystals (about 203 parts by weight, with a purity of 99.9942 wt %) and a liquid phase (about 960 parts by weight).

The quality of the obtained caprolactam product was analyzed, the analysis results showed that the purity of the caprolactam was 99.9956 wt %, the PM value was 39600 s, the VB was 0.032 mmol/kg, the E value was 0.026, the chromatic value was 0, and the alkalinity was 0.02 mmol/kg.

1-methoxy-1,4-cyclohexadiene, N,N-dimethylaniline, 2,5-dimethylaniline, 2,6-dimethylaniline and 2-methylaniline, the corresponding content of these by-products is 0.8%.

By adopting ethanol as a reaction solvent, the distribution of by-products are more desirable, the content of light components is increased, and the content of heavy components is obviously reduced. Both the types and the quantity of the byproducts adjacent to the caprolactam (CPL) are reduced, and the method is favorable for removing or co-producing certain by-products. The primary and common by-products of the gas phase rearrangement are hexanenitrile, cyclohexenone, 5-cyano-pentene-1, cyclohexanone, cyanocyclopentane; when ethanol is used as the reaction solvent, the content of these by-products rises from 2.0% to 2.7%. Meanwhile, the content of other by-products is reduced by 1.7%, it is very conducive to separation, purification and refinement of the CPL.

If ethanol is used as a reaction solvent, the catalyst has no induction period, the selectivity of CPL is quickly raised to about 95.5%, and the total selectivity of CPL can be increased by 0.4%.

TABLE 1

(The solvent in the gas phase Beckmann rearrangement reaction was ethanol)

| Reaction time h | Cyclohexanone oxime conversion rate % m | Selectivity of caprolactam % m | AEH % m | Capro-nitrile % m | Cyclo-hexanone % m | Pentene-1 % m | Cyano-cyclopentane % m | Cyclo-hexenone % m | Ethoxycyclo-hexanone % m | N-ethyl-CPL % m | 25.5 % m | Other % m |
|---|---|---|---|---|---|---|---|---|---|---|---|---|
| 5-22 | 99.92 | 95.65 | 0.88 | 0.13 | 0.53 | 0.95 | 0.39 | 0.46 | 0.13 | 0.13 | 0.14 | 0.61 |
| 22-29 | 99.91 | 95.73 | 0.92 | 0.11 | 0.54 | 0.90 | 0.40 | 0.40 | 0.11 | 0.12 | 0.13 | 0.64 |
| 29-46 | 99.91 | 95.84 | 0.93 | 0.10 | 0.58 | 0.88 | 0.44 | 0.40 | 0.11 | 0.11 | 0.12 | 0.49 |

TABLE 2

(Gas phase Beckmann rearrangement with methanol as solvent)

| Reaction time h | Conversion rate of Cyclohexanone oxime % m | Selectivity of caprolactam % m | AMH % m | Methyl-hexenoate % m | Hexane-nitrile % m | Cyclo-hexanone % m | Pentene-1 % m | Cyano-cyclo-pentane % m | Cyclo-hexenone % m | Methoxy-cyclo-hexanone % m | N-ethyl-CPL % m | 25.5 % m | Other % m |
|---|---|---|---|---|---|---|---|---|---|---|---|---|---|
| 5-22 | 99.90 | 95.06 | 1.00 | 0.30 | 0.18 | 0.51 | 0.84 | 0.20 | 0.37 | 0.20 | 0.23 | 0.19 | 0.92 |
| 22-29 | 99.90 | 95.33 | 1.03 | 0.26 | 0.18 | 0.52 | 0.82 | 0.21 | 0.30 | 0.19 | 0.19 | 0.16 | 0.81 |
| 22-46 | 99.88 | 95.35 | 1.06 | 0.24 | 0.19 | 0.54 | 0.78 | 0.26 | 0.24 | 0.19 | 0.17 | 0.14 | 0.84 |

When comparing the Table 1 with the Table 2, the ethanol significantly inhibits the side reaction in which the solvent participates, regardless of the type of the by-products or the content of the by-products, the by-products obtained by using different solvents have obvious differences.

The variety and the amount of the by-products containing ethyl are obviously reduced, the by-products containing ethyl mainly comprise 2-ethoxy-cyclohexanone, N-ethyl-caprolactam, ethyl-caprolactam and the like, 5-hexenoic acid ethyl ester is not found, and the content of the by-products is 0.2%; there are a great variety of by-products corresponding to methyl-containing compounds, the by-products containing methyl mainly comprise 4-hexenoic acid methyl ester, 5-hexenoic acid methyl ester, 2-methyl-cyclopentanone, 2-methoxy-cyclohexanone, 3-methoxy-cyclohexanone, N-methyl-aniline, methyl-caprolactam, N-methyl-caprolactam, O-methyl-epsilon-caprolactam and the like, and also contains a trace amount of methyl by-products, such as 2-methacrylonitrile, 4-methylpentanonitrile, 2-methylpyridine, 1-methoxy-1,3-cyclohexadiene, Methanol is more active and more prone to side reactions than ethanol.

Table 1 and Table 2 further illustrate that, among other non-listed by-products, the content of non-listed by-products obtained by using methanol as a reaction solvent is significantly higher than that of non-listed by-products obtained by using ethanol as a reaction solvent.

The preparation method of caprolactam provided by the present disclosure adopts specific steps, and ethanol is used in both a solvent of gas phase Beckmann rearrangement reaction of cyclohexanone oxime and a crystallization solvent during a crystallization process, such that the selectivity of caprolactam is higher, the types and the contents of byproducts are reduced, thus the ethanol is more conducive to improving the yield and quality of caprolactam. Preferably, the catalyst preparation process related to the present disclosure also uses ethanol, which not only can improve stability of the catalyst and further improve the yield and quality of caprolactam, but also may recover ethanol in the catalyst preparation process for providing at least part of ethanol in step (1) and/or at least part of ethanol in the crystallization solvent in step (4), thereby further improving the economic efficiency of the whole process.

The preferred embodiments of the present disclosure have been described above in detail, but the present disclosure is not limited thereto. Within the scope of the technical idea of the present disclosure, many simple modifications can be made to the technical solution of the present disclosure, including various technical features being combined in any other suitable way, and these simple modifications and combinations should also be regarded as the disclosure of the present disclosure, and all fall within the scope of the present disclosure.

The invention claimed is:

1. A method for preparing caprolactam comprising the following steps:
   (1) contacting cyclohexanone oxime with a catalyst to carry out reaction in the presence of ethanol and under the condition of gas phase Beckmann rearrangement reaction of cyclohexanone oxime;
   (2) separating the reaction product obtained in step (1) to produce an ethanol solution of crude caprolactam, and then separating the ethanol solution of crude caprolactam to obtain ethanol and crude caprolactam;
   (3) removing impurities with boiling points lower than that of caprolactam in the crude caprolactam to obtain a light component removal product;
   (4) mixing the light component removal product with a crystallization solvent to carry out crystallization and solid-liquid separation to obtain a crystalline crystal; and
   (5) subjecting the crystalline crystal to a hydrogenation reaction;
   wherein the crystallization solvent contains 0.1-2 wt % of ethanol.

2. The method of claim 1, wherein the cyclohexanone oxime in step (1) accounts for 20-50 wt % of the sum of cyclohexanone oxime and ethanol; and/or
   the reaction in step (1) is performed in the presence of ethanol and water, wherein water accounts for 0.1-3 wt % of the total amount of water, ethanol and cyclohexanone oxime; and/or
   an inert gas is used as a carrier gas in the reaction of step (1), and the molar ratio of the inert gas relative to cyclohexanone oxime is 0.5-50:1.

3. The method of claim 1, wherein the conditions of gas phase Beckmann rearrangement reaction comprise: temperature is within a range of 350-400° C., the pressure is within a range of 0.005-0.81 MPa, the weight hourly space velocity of the cyclohexanone oxime is within a range of 0.1-10h$^{-1}$; and/or
   the conversion rate of cyclohexanone oxime in the reaction of step (1) is not lower than 99.5 wt %.

4. The method of claim 1, wherein the catalyst comprises a binder and a silicon molecular sieve having a MFI topological structure; the catalyst comprises 50-95 wt % of the molecular sieve based on the dry weight and 5-50 wt % of the binder in terms of oxide, based on the dry weight of the catalyst; or
   the molecular sieve contains metal elements, and ions of the metal elements have a Lewis acid characteristic; the content of the metal element in the molecular sieve is 5-10011 μg/g, based on the total amount of the molecular sieve.

5. The method of claim 4, wherein the metal element is at least one selected from the group consisting of transition metal elements, group IIIA elements, and group IVA elements;
   the transition metal element is at least one selected from the group consisting of group IB, group JIB, group IVB, group VB, group VIB, group VIIB, and group VIII metal elements; and/or
   the content of the metal elements in the molecular sieve is 6-90 μg/g, based on the total amount of the molecular sieve; and/or
   the molecular sieve has a BET specific surface area within a range of 400-500 m$^2$/g, a crystalline grain particle size within a range of 0.1-0.3 μm, and an external specific surface area within a range of 30-60 m$^2$/g.

6. The method of claim 5, wherein the metal element is at least one selected from the group consisting of elements Al, Ga, Ge, Ag, Co, Ni, Cu, Zn, Mn, Pd, Pt, Cr, Fe, Au, Ru, Rh, Ti, Zr, V, Mo and W; and/or
   the binder is silicon oxide.

7. The method of claim 5, wherein the metal elements have an ionic valence of +3 and/or an ionic valence of +4.

8. The method of claim 4, wherein a preparation method of the catalyst comprises the following steps:
   (a-1) mixing ethyl orthosilicate, ethanol, a metal source, tetrapropylammonium hydroxide with water to obtain a colloid mixture; wherein the molar ratio of ethyl orthosilicate calculated by SiO$_2$, ethanol, tetrapropylammonium hydroxide and water is 1: (4-25): (0.06-0.45): (6-100); the weight ratio of the ethyl orthosilicate calculated by SiO$_2$ relative to the metal source calculated by the metal element is (10,000-200,000): 1;
   (a-2) subjecting the colloid mixture to a two-stage crystallization with an ethanol-hydrothermal system under variable temperatures, wherein the conditions of the two-stage crystallization with an ethanol-hydrothermal system under variable temperatures comprise: crystallizing at 40-80° C. for 0.5-5 days, and then crystallizing at 80-130° C. for 0.5-5 days;
   (a-3) concentrating the crystallization mother liquor obtained in step (a-2) to obtain a molecular sieve slurry;
   (a-4) blending the molecular sieve slurry with a binder and pulping to obtain a molecular sieve-binder slurry; subjecting the molecular sieve-binder slurry to a mist spray forming, and then roasting; and
   (a-5) contacting the roasted product of step (a-4) with an alkaline buffer solution of a nitrogen-containing compound, and subsequently carrying out drying.

9. The method of claim 8, wherein the metal source is at least one selected from the group consisting of a nitrate of the metal, a chloride of the metal, a sulfate of the metal, an acetate of the metal, and an ester metal compound; and/or
   the conditions of the mist spray forming in step (a-4) comprise: the inlet temperature is within a range of 180-240° C., the outlet temperature is within a range of 80-120° C.; and/or
   the ethanol in the crystallization mother liquor of step (a-3) is recovered to provide at least part of the ethanol of step (1) and/or at least part of the ethanol of the crystallization solvent of step (4).

10. The method of claim 4, wherein the preparation method of the catalyst comprises the following steps:
    (b-1) mixing ethyl orthosilicate, ethanol, a metal source, tetrapropylammonium hydroxide and water to obtain a colloid mixture; wherein the molar ratio of ethyl orthosilicate calculated by SiO$_2$, ethanol, tetrapropylammonium hydroxide and water is 1: (4-25): (0.06-0.45):

(6-100); the weight ratio of the ethyl orthosilicate calculated by $SiO_2$ relative to the metal source calculated by the metal element is (10,000-200,000): 1;

(b-2) subjecting the colloid mixture to a two-stage crystallization with an ethanol-hydrothermal system under variable temperatures, wherein the conditions of the two-stage crystallization with an ethanol-hydrothermal system under variable temperatures comprise: crystallizing at 40-80° C. for 0.5-5 days, and crystallizing at 80-130° C. for 0.5-5 days;

(b-3) sequentially filtering and drying the crystallization mother liquor obtained in step (b-2) to obtain a molecular sieve raw powder;

(b-4) crushing the molecular sieve raw powder, blending the crushed molecular sieve raw powder with a binder, and then carrying out rotary molding to obtain spherical particles; and (b-5) roasting the spherical particles, contacting the roasted spherical particles with an alkaline buffer solution containing a nitrogen compound, and subsequently carrying out drying.

11. The method of claim 10, wherein the metal source is at least one selected from the group consisting of a nitrate of the metal, a chloride of the metal, a sulfate of the metal, an acetate of the metal, and an ester metal compound; and/or in step (b-4), the molecular sieve raw powder is pulverized to 100-1,000 meshes; the conditions of the rotary molding comprise: the rotary table inclination angle within a range of the relationship between the rotary table diameter D and the rotary table depth H is H=0.1-0.3D, and the rotation speed of the rotary table is within a range of 10-50 rpm; and/or the ethanol in the crystallization mother liquor of step (b-3) is recovered to provide at least part of the ethanol of step (1) and/or at least part of the ethanol of the crystallization solvent of step (4).

12. The method of claim 8, wherein the conditions of the two-stage crystallization with an ethanol-hydrothermal system under variable temperatures comprise: crystallizing at 50-80° C. for 1-1.5 days, and crystallizing at 100-120° C. for 1.5-2 days; and/or the roasting conditions comprise: the temperature is within a range of 200-600° C., and the time is within a range of 1-20h; and/or the contacting conditions comprise: the temperature is within a range of 50-120° C., the pressure is within a range of 0.5-10 kg/cm², the time is within a range of 0.1-5h.

13. The method of claim 8, wherein the alkaline buffer solution of a nitrogen-containing compound comprises an ammonium salt and an alkali, the ammonium salt is contained in an amount of 0.1-20 wt %, the alkali is contained in an amount of 5-30 wt %, and the alkaline buffer solution of a nitrogen-containing compound has a pH within a range of 8.5-13.5; and/or the alkaline buffer solution of a nitrogen-containing compound is used in an amount of 500-1,500 parts by weight relative to 100 parts by weight of the roasted product on a dry basis.

14. The method of claim 1, wherein in step (2), the reaction product obtained in step (1) is subjected to a gas-liquid separation to obtain an ethanol solution of the crude caprolactam and a gas phase material flow; and the ethanol solution of the crude caprolactam is subjected to distillation to obtain ethanol and crude caprolactam.

15. The method of claim 1, wherein the method further comprises: dehydrating the ethanol to obtain an anhydrous ethanol; the ethanol and/or anhydrous ethanol is used for providing at least part of the ethanol in step (1) and/or at least part of the ethanol in the crystallization solvent in step (4); and/or the used amount of the crystallization solvent in step (4) is 150-400 parts by weight, relative to 100 parts by weight of the light component removal product; and/or the crystallization temperature is within a range of 10-65° C.

16. The method of claim 1, wherein the crystallization solvent comprises ethanol, a solvent A and optionally a solvent B; the solubility of caprolactam in the solvent A and solvent B is less than 5 wt % at 20° C., and the solubility of caprolactam in the solvent A is larger than the solubility of caprolactam in the solvent B.

17. The method of claim 16, wherein the content of ethanol in the crystallization solvent is within a range of 0.5-2 wt %; and/or the content of solvent B in the crystallization solvent is within a range of 1-35 wt %.

18. The method of claim 16, wherein the solvent A is selected from ethers having 2-8 carbon atoms, and the solvent B is selected from alkanes having 6-12 carbon atoms.

19. The method of claim 18, wherein the solvent A is one selected from the group consisting of methyl ethyl ether, diethyl ether, n-propyl ether, isopropyl ether, n-butyl ether, isobutyl ether, ethylene glycol dimethyl ether, vinyl ether, methyl tert-butyl ether and ethyl tert-butyl ether; and the solvent B is at least one selected from the group consisting of n-hexane, n-heptane, n-octane, n-nonane, methylhexane, isohexane, neohexane, cyclohexane, methylcyclopentane, methylcyclohexane, isoheptane, isooctane and isononane.

20. The method of claim 1, wherein the hydrogenation reaction of step (5) is performed in the presence of water and in the presence of a hydrogenation catalyst; the crystalline crystal accounts for 60-90 wt % of the total amount of crystalline crystals and water; and the conditions of the hydrogenation reaction comprise: the temperature is within a range of 50-150° C.; the pressure is within a range of 0.2-1.5 MPa.

21. The method of claim 4, wherein the metal element is Ce and the binder is a silicon oxide.

* * * * *